(12) United States Patent
Khomenko et al.

(10) Patent No.: US 10,527,543 B2
(45) Date of Patent: Jan. 7, 2020

(54) OPTICAL CHARACTERIZATION OF FIBER REINFORCED PLASTIC COMPOSITES BASED ON OPTICAL TRANSMISSION SCANNING

(71) Applicant: General Photonics Corporation, Chino, CA (US)

(72) Inventors: Anton Khomenko, Ontario, CA (US); Xiaotian Steve Yao, Diamond Bar, CA (US); Oleksii Karpenko, Lansing, MI (US); Xiaojun James Chen, San Gabriel, CA (US)

(73) Assignee: General Photonics Corporation, Chino, CA (US)

( * ) Notice: Subject to any disclaimer, the term of this patent is extended or adjusted under 35 U.S.C. 154(b) by 0 days.

(21) Appl. No.: 15/905,755

(22) Filed: Feb. 26, 2018

(65) Prior Publication Data
US 2018/0348126 A1 Dec. 6, 2018

Related U.S. Application Data

(60) Provisional application No. 62/463,254, filed on Feb. 24, 2017.

(51) Int. Cl.
*G01N 21/47* (2006.01)
*G01N 21/958* (2006.01)
*G01N 21/84* (2006.01)

(52) U.S. Cl.
CPC ....... *G01N 21/474* (2013.01); *G01N 21/4795* (2013.01); *G01N 21/958* (2013.01); *G01N 2021/4707* (2013.01); *G01N 2021/4735* (2013.01); *G01N 2021/4742* (2013.01); *G01N 2021/4773* (2013.01); *G01N 2021/4797* (2013.01); *G01N 2021/8472* (2013.01)

(58) Field of Classification Search
CPC ... G01N 2021/4735; G01N 2021/4742; G01N 21/474; G01N 2021/4707; G01N 2021/4773; G01N 2021/4797; G01N 2021/8472; G01N 21/4795; G01N 21/958
See application file for complete search history.

(56) References Cited

U.S. PATENT DOCUMENTS

2010/0149532 A1* 6/2010 Moriya ................. G01N 11/00
356/336

* cited by examiner

*Primary Examiner* — Tri T Ton
(74) *Attorney, Agent, or Firm* — Perkins Coie LLP

(57) ABSTRACT

The technology disclosed in this application provide for non-destructive and non-contact optical characterization of fiber reinforced plastic composites and other structures under test based on optical transmission scanning.

20 Claims, 12 Drawing Sheets

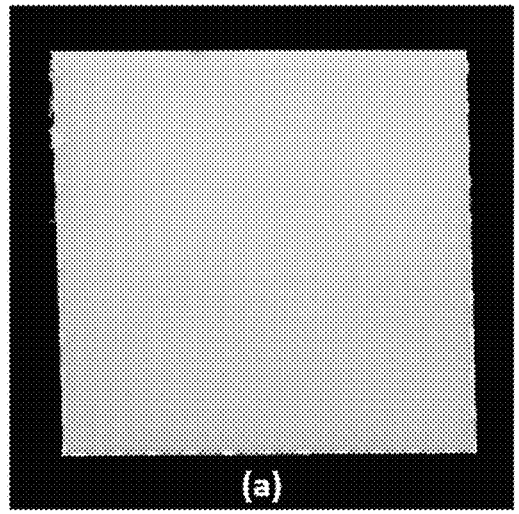
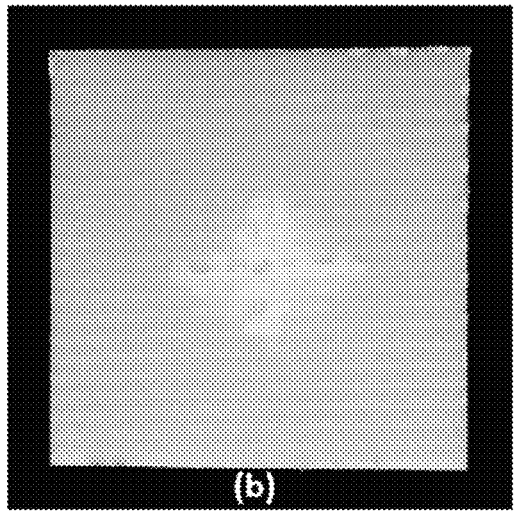
FIG. 3A　　　　　　　　　　　FIG. 3B
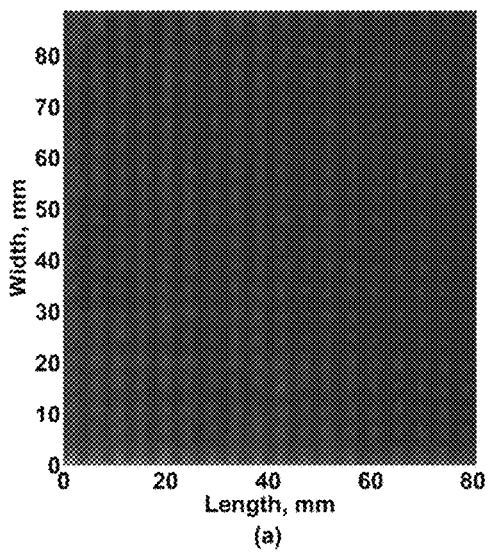
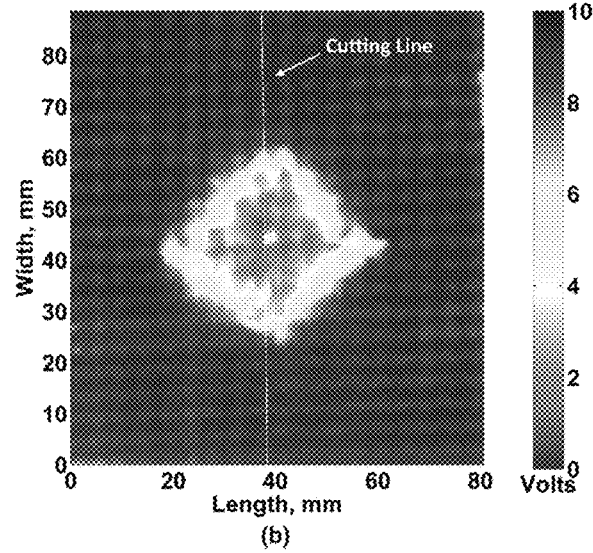
FIG. 4A　　　　　　　　　　　FIG. 4B

OPTICAL CHARACTERIZATION OF FIBER REINFORCED PLASTIC COMPOSITES BASED ON OPTICAL TRANSMISSION SCANNING

PRIORITY CLAIM AND CROSS-REFERENCE TO RELATED APPLICATION(S)

This reference claims the benefits of and the priority to U.S. Provisional Application No. 62/463,254, entitled "OPTICAL CHARACTERIZATION OF FIBER REINFORCED PLASTIC COMPOSITES BASED ON OPTICAL TRANSMISSION SCANNING" and filed Feb. 24, 2017, which is incorporated by reference as part of this patent document for all purposes.

TECHNICAL FIELD

This patent document relates to optical sensing of objects and materials.

BACKGROUND

Non-destructive evaluation (NDE) techniques are techniques or methods for testing or inspecting an object or material without damaging or alternating the object or material and are often preferred in measuring and evaluating structural and other properties of objects and materials.

Some examples of existing NDE techniques to inspect fiber reinforced polymer (FRP) composite materials are ultrasonic testing (UT), X-ray radiography and tomography, infrared (IR) thermography or digital image correlation (DIC) with visible range radiation. Depending on the need or requirements of a particular application, each of these methods may have its own advantages and limitations.

For example, a phased array UT may be used to furnish precise information about the location of damage and its spatial distribution inside a glass fiber reinforced polymer (GFRP) laminate structure. However, phased arrays require coupling with the test specimen, and they can be rather complex and costly because sophisticated electronics are needed to adjust the time delays between the piezoelectric transducers for proper focusing of the wave energy at the defect site. Hence, relatively simpler systems for immersed and air coupled UT with a single transducer have been routinely used for NDE of composite structures.

For another example, X-ray computed tomography (CT) can provide detailed images of delaminations and other defects in composites. However, X-ray CT uses relatively high levels of ionizing radiation, which can be dangerous for inspectors. Moreover, chamber volume for X-ray CT severely limits the size of the sample which can be evaluated.

IR thermography may be suitable for rapid screening of large components, but it provides little information about the volumetric distribution of damage.

SUMMARY

This patent document discloses techniques and devices for performing non-destructive evaluation (NDE) of a target sample based on optical transmission measurements.

In one aspect, the disclosed technology can be implemented to provide a method for performing non-destructive evaluation (NDE) of a target sample based on optical transmission measurements to include directing probe light to transmit through a target sample to produce transmitted probe light; using an optical detector to receive the transmitted probe light and to measure optical transmission of the target sample; scanning a relative position between the target sample and the probe light to direct the probe light to transmit through the target sample at different locations of the target sample to obtain measurements of optical transmission of the target sample at the different locations as a result of the scanning; discriminating measurements of optical transmission of the target sample at the different locations produced by ballistic photons that transmit through the target sample along a straight line and by scattered photons that transmit through the target sample by being scattered away from a straight line; and processing the measurements of optical transmission of the target sample at the different locations produced by ballistic photons and by scattered photons to extract information on a structural pattern distribution in the target sample.

In another aspect, the disclosed technology can be implemented to provide a method for performing non-destructive evaluation (NDE) of a target sample on optical transmission measurements to include directing probe light at different optical inspection wavelengths to transmit through a target sample to produce transmitted probe light at the different optical inspection wavelengths; using an optical detector to receive the transmitted probe light at the different optical inspection wavelengths and to measure optical transmission of the target sample at the different optical inspection wavelengths; scanning a relative position between the target sample and the probe light to direct the probe light to transmit through the target sample at different locations of the target sample to obtain measurements of optical transmission of the target sample at the different optical inspection wavelengths and at the different locations as a result of the scanning; and processing measurements of optical transmission of the target sample at the different locations and at the different optical inspection wavelengths to extract information on a structural pattern distribution in the target sample.

In one aspect, the disclosed technology can be implemented to provide a method for performing non-destructive evaluation (NDE) of a target sample on optical transmission measurements to include directing probe light to transmit through a target sample to produce transmitted probe light; using an optical detector to receive the transmitted probe light and to measure optical transmission of the target sample; scanning a relative position between the target sample and the probe light to direct the probe light to transmit through the target sample at different locations of the target sample to obtain measurements of optical transmission of the target sample at the different locations as a result of the scanning; controlling optical focusing of the probe light along a propagation path of the probe light at the target sample during the scanning; and processing measurements of optical transmission of the target sample at the different locations and different optical focusing to extract information on a 3-dimensional structural pattern distribution in the target sample in two directions caused by the scanning and in the propagation path of the probe light at the target sample caused by the optical focusing.

In one aspect, the disclosed technology can be implemented to provide a method for performing non-destructive evaluation (NDE) of a target sample on optical transmission measurements to include directing probe light to transmit through a target sample to produce transmitted probe light; operating an input optical polarization device in an optical path of the probe light prior to the target sample and an output optical polarization device in an optical path of the transmitted probe light after the target sample; using an optical detector to receive the transmitted probe light and to measure optical transmission of the target sample in connection with operations of the input and output optical polarization devices; scanning a relative position between the target sample and the probe light to direct the probe light to transmit through the target sample at different locations of the target sample to obtain measurements of optical transmission of the target sample at the different locations as a result of the scanning and operations of the input and output optical polarization devices; and processing measurements of optical transmission of the target sample at the different locations to extract information on a structural pattern distribution in the target sample and optical retardation measurements caused by the target sample at the different locations.

The above and other aspects of the disclosed technology and their implementations are described in greater detail in the drawings, the description and the claims

BRIEF DESCRIPTION OF DRAWINGS

FIG. 3A shows a glass fiber reinforced polymer composite sample without damage induced by impact.

FIG. 3B shows a glass fiber reinforced polymer composite sample with damage induced by impact.

FIG. 4A shows an OT-scan of a healthy GFRP sample.

FIG. 4B shows an OT-scan of the GFRP sample after E=20 J impact.

DETAILED DESCRIPTION

Figure 1:
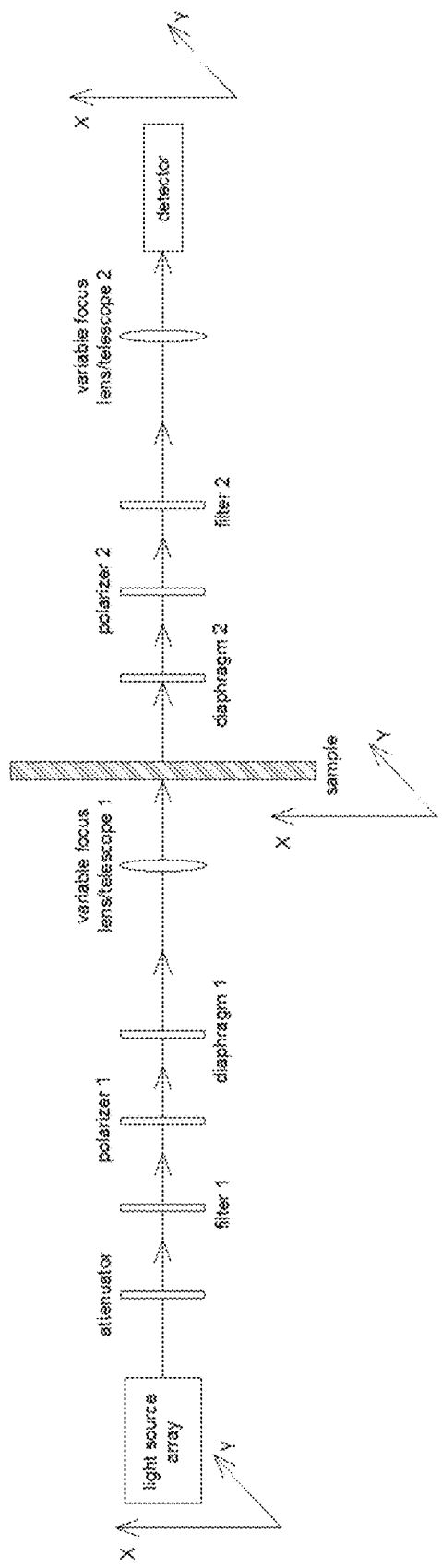
FIGS. 1 and 2 show examples of an optical transmission scanning (OTS) system for measuring a target sample such as fiber reinforced polymer (FRP) composites and other materials or objects.

The technology disclosed in this application can be used for optical characterization of fiber reinforced plastic composites based on optical transmission scanning (OTS) in various materials, media or structures to be measured by detection of optical transmission of probe light, including fiber reinforced polymer (FRP) composites such as glass or aramid FRP composites. When a material is illuminated by probe light, the probe light interacts with the material and the light-material interactions may be reflected in different ways such as optical transmission, optical absorption, optical reflection, or optical scattering of the incident probe light. The technology disclosed in this application is directed to detection and measurements of optical transmission of probe light at one or more probe optical wavelengths that passes through a target material under measurement to extract structural information and certain properties of the target material without damaging or alternating the target material and without making physical contact with the target material. Therefore, the disclosed optical transmission scanning (OTS) technology is a non-destructive evaluation (NDE) technique and can be used to provide unique features when compared to some other NDE methods such as ultrasound testing (UT) and X-ray computed tomography (CT) for evaluating FRP composites that can be expensive, and may require direct contacts.

In the disclosed optical transmission scanning (OTS) technology, the measured optical transmission of the incident probe light through the target material includes the transmitted probe light represented by (1) ballistic photons that transmit through the target material along a straight line and (2) scattered photons that transmit through the target material by being scattered in directions that deviate from a straight line. Certain properties, including spatial and temporal properties, of the optical transmission of the probe light are measured and processed to extract desired structural information and material properties of the target material.

Fiber reinforced polymer (FRP) composites can be used for many applications due to the multitude of benefits they offer, such as light weight, high specific stiffness, high specific strength, and good resistance to chemical agents. Combined with design flexibility and strategic tailoring of mechanical properties, these key advantages have propelled the wide acceptance of FRP composites in different industries, including, e.g., marine, automotive, aerospace, sporting, construction industries. Typical examples of semi-transparent FRP composites include, but not limited to: glass fiber reinforced polymer (GFRP) and aramid/Kevlar fiber reinforced polymer (A/KFRP) composites. However, the increasing use of advanced multi-component materials brings along major challenges. FRP composites are vulnerable to flaws during fabrication and operation, which could lead to premature failure of structural components.

The elastic behavior and fracture of FRP composites largely depend on the mechanical properties of the fibers and the matrix, the strategic stacking sequence of layers, and the selection of weave patterns. Anisotropy and mismatch of material properties at the interlaminar interfaces are roots for many flaws. For instance, a laminated structure subjected to a low velocity impact, such as a tool drop, may develop delaminations between the inner layers that are not visible on the surface. Hence, non-destructive evaluation (NDE) techniques that can measure both surface and subsurface defects are desirable in evaluating the integrity of FRP composite structures during their service lives.

Optical inspection methods are generally non-invasive, safe, non-contacting, sensitive, whole-field, and inexpensive and are often used in biomedical applications to evaluate the properties of biological tissues. Some optical techniques initially designed for medical imaging can be adapted for NDE of semi-transparent FRP composites. Examples of optical NDE techniques for testing semi-transparent FRP laminates include electronic shearography, digital speckle pattern interferometry (DSPI), digital image correlation (DIC), digital holography (DH), and optical coherence tomography (OCT). These approaches can be used for locating defects and studying the mechanical behavior of semi-transparent FRP composites. One of the limitations of shearography, DSPI, DH, and DIC techniques is that thermal or mechanical loading of the test specimen is required to create a displacement field which may cause a structural damage.

Both time domain (TD) and Fourier domain (FD) OCT techniques are based on detecting or registering back-scattered and back-reflected radiation; and have been used to study internal structure, defects, and stress in semi-transparent FRP structures. Various implementations of TD OCT and FD OCT tend to have a limited penetration depth inside the FRP specimens, e.g., only a few millimeters, due to very strong scattering inside most composite structures.

The disclosed optical transmission scanning (OTS) technology in this patent document can be implemented to include features of ballistic scanners for detecting ballistic photons that transmit through the tissue along straight transmission paths to measure the full depth of a target material. Since many fibers (e.g., glass and aramid) and epoxy resins exhibit good optical transmission properties in the visible spectral range, a similar principle was employed for NDE of semi-transparent FRP composites (GFRP was used as the test specimen). Similar principle and algorithm applies for other materials and inspection wavelengths, i.e., the composite material must be less than 100% opaque for inspection radiation, which is not necessary in the visible range.

This patent document discloses specific examples of NDE methods based on optical transmission scanning (OTS) for quantitative characterization of semi-transparent FRP (GFRP) samples. The disclosed OTS techniques may also be used for inspection and characterization of other materials and structures.

Examples of Materials and Methods Used in Tests

In conducted tests for the disclosed OTS techniques semi-transparent FRP composites were used. Such GFRP composite samples were manufactured using a vacuum-assisted liquid molding process. The reinforcement was S2-glass plain weave fabric with areal weight of 818 g/m$^2$, namely ShieldStrand® S, provided by Owens Corning. The GFRP samples comprised eight layers of such fabric stacked at the same angle. The distribution medium was Resinflow 60 LDPE/HDPE blend fabric from Airtech Advanced Materials Group. The resin was SC-15, a two part toughened epoxy obtained from Applied Poleramic. The GFRP plate (508.0×609.6 mm) was manufactured in a 609.6×914.4 mm aluminum mold with point injection and point venting. After the materials were placed, the mold was sealed using a vacuum bag and sealant tape, and it was then infused under vacuum at 29 in Hg. The resin-infused panel was cured in a convection oven at 60° C. for two hours and post-cured at 94° C. for four hours. Finally, impact samples with dimensions of 100×100×4.7 mm were cut from the manufactured GFRP plate using a diamond saw.

Elastic properties of the orthotropic GFRP samples used in experimental study were determined from tensile tests, and are presented in Table 1 below.

TABLE 1

| Elastic constants of GFRP laminate. | | | | | | | | |
|---|---|---|---|---|---|---|---|---|
| $E_{11}$, GPa | $E_{22}$, GPa | $E_{33}$, GPa | $G_{13}$, GPa | $G_{23}$, GPa | $G_{12}$, GPa | $v_{13}$ | $v_{23}$ | $v_{12}$ |
| 23.1 | 23.1 | 6.9 | 2.54 | 2.54 | 3.2 | 0.28 | 0.28 | 0.36 |

The refractive index of manufactured GFRP sample can be calculated using the rule of mixtures for the resin and the fiber volumes as:

$$n_{composite} = n_{resin} \cdot V_{resin} + n_{fiber} \cdot V_{fiber}, \quad (1)$$

where $n_{resin}$ and $n_{fiber}$ are the refractive indices of resin and fiber, respectively; and $V_{resin}$ and $V_{fiber}$ are the volume fractions of resin and fiber, respectively. SC-15 is a combination of bisphenol A diglycidyl ether resin and cycloaliphatic amine curing agent with weight fractions of ~0.77 (100/130) and ~0.23 (30/130), respectively [27]. Weight fractions can be converted to volume fractions using the following relation:

$$\frac{V_{epoxy}}{V_{hardener}} = \frac{\left(\frac{m_{epoxy} \cdot \rho_{hardener}}{m_{epoxy} \cdot \rho_{hardener} + m_{hardener} \cdot \rho_{epoxy}}\right)}{\left(\frac{m_{hardener} \cdot \rho_{epoxy}}{m_{epoxy} \cdot \rho_{hardener} + m_{hardener} \cdot \rho_{epoxy}}\right)}, \quad (2)$$

where $m_{epoxy}$ and $m_{hardener}$ are the weight fractions of epoxy and hardener, and $\rho_{epoxy}$ and $\rho_{hardener}$ are the densities of epoxy and hardener, respectively. Using Equation 2, the $V_{epoxy}$ and $V_{hardener}$ For SC-15 can be calculated as ~0.75 (105/141) and ~0.25 (36/141), respectively. Also, density of SC-15 can be calculated as $$\rho_{resin} = \rho_{hardener} \cdot \frac{V_{hardener}}{m_{hardener}} = \rho_{epoxy} \cdot \frac{V_{epoxy}}{m_{epoxy}},$$

i.e., $\rho_{resin}$~1160·kg/m$^3$.

The refractive index of bisphenol A diglycidyl ether resin is $n_{epoxy}$~1.574, and average refractive index of cycloaliphatic amine hardener is $n_{hardener}$~1.5. Hence, according to Equation 1, refractive index of uncured SC-15 can be estimated as $n_{resin}$~1.556. Density and refractive index of S-glass fiber is 2480-2490 kg/m$^3$ and 1.523, respectively. The weight fraction of resin in manufactured GFRP composite is 0.365. Using Equation 2, volume fractions of resin and glass fibers can be found as ~0.55 and ~0.45, respectively. According to Equation 1, the refractive index of resulting GFRP composite can be estimated as $n_{composite} \sim 1.541$. The refractive index of the resulting composite depends on many factors, such as the inspection wavelength, curing conditions, or the working environment.

The linear attenuation of GFRP composite material was measured with 1.7 mW incident radiation power for 4, 8, and 16 layer laminates with the average thickness of 2.6, 4.6, and 9.2 mm, respectively. In general, for collimated monochromatic radiation in homogeneous media, the power of the transmitted radiation can be calculated using the Beer-Lambert law:

$$P_{as} = P_0 \cdot T_{as} = P_0 \cdot \exp\left[-\sum_{i=1}^{M} (\mu_a^i + \mu_s^i) \cdot l_i\right] = P_0 \cdot \exp\left[-\sum_{i=1}^{M} \mu^i \cdot l_i\right], \quad (3)$$

where $P_{as}$ is the transmitted radiation power that is attenuated by the local material in its pristine state; $P_0$ is the incident radiation power; $T_{as}$ is the transmission coefficient, which accounts only for absorption and scattering in the test specimen in the absence of reflections from its interlaminar interfaces; M is the number of attenuating species of the material sample; $\mu_a^i$, $\mu_s^i$, and $\mu^i$ are the absorption coefficient, scattering coefficient, and linear attenuation coefficient, respectively; and $l_i$ is the thickness of ith specie. The transmitted radiation power for 4, 8, and 16 layer GFRP laminates corresponded to 8.99, 5.22, and 1.52 V output from the receiving photodetector. Thus, from the ratios of the photodetector outputs corresponding to GFRP samples with different thickness, a linear attenuation coefficient was found to be $\sim 2.7$ cm$^{-1}$. Generally, at a given incident power and signal to noise ratio (SNR), this value determines the maximum thickness of GFRP composite which can be evaluated using an OTS system.

The GFRP composite samples used in OTS tests were subject to drop-weight impact tests to induce structural defects in the samples for the OTS measurements. The drop-weight tests were performed according to the ASTM D7136 standard using an Instron 9250 HV Dynatup machine that was equipped with an 88.96 kN load cell impactor, a velocity detector, and a pneumatic brake to prevent multiple impacts. The edges of the GFRP specimen were clamped by pneumatically assisted grips. The exposed diameter of the composite plate for impact loading was 76.2 mm, as per ASTM D7136. A 12.7-mm diameter hemispherical head impactor was used for the impact testing. Three GFRP specimens were impacted with 20 J energy for subsequent NDE by the OTS system.

Examples of Optical Transmission Scanning (OTS) System

Figure 2:
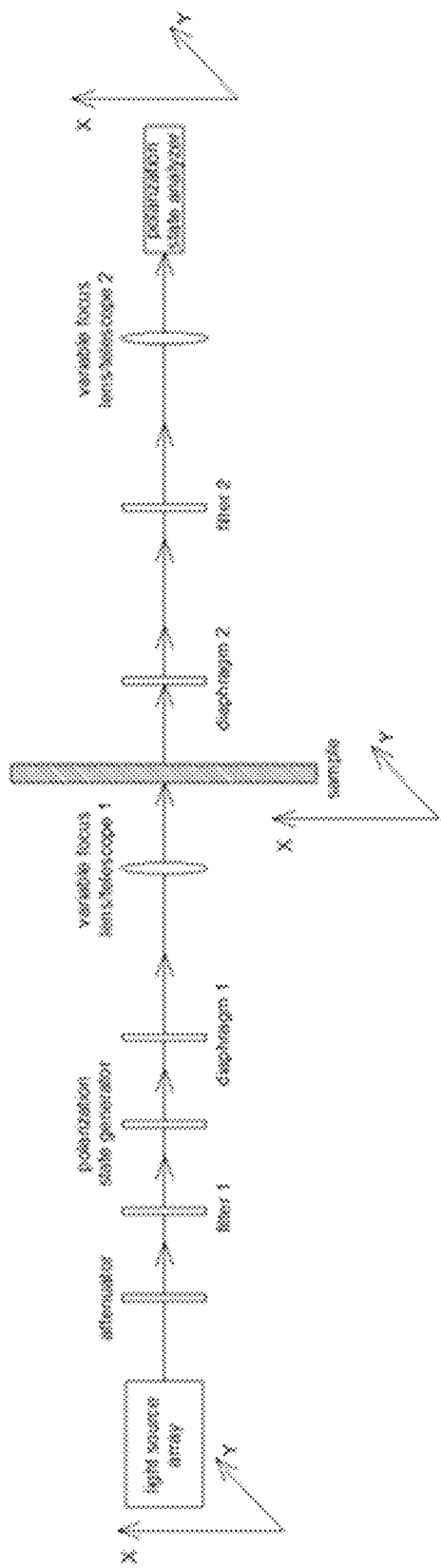

FIGS. 1 and 2 show examples of an OTS system based on the disclosed technology. Each illustrated OTS uses a light source that generates collimated or focused probe optical radiation at a single or array of fixed probe wavelengths and may also include one or more tunable light sources. Such a light source can be a point light source, a line light source, or a plane light source and may operate in UV, visible, near-IR, or IR ranges. Examples of suitable light sources include lamps (including UV, visible, and IR), broad spectrum source (e.g., superluminescent diode, white light, or ultrafast laser, which can be fiber, solid state, or gas laser, etc.), diode laser, IR emitters, etc. This OTS system includes an input optical module that directs the probe light from the light source onto a target sample and an output optical module that collects the transmitted probe light from the target sample and direct the collected probe transmission to an optical detector for detection and analysis. A scanning mechanism is provided to scan a relative position between the target sample and the probe light from the input optical module to direct the probe light to transmit through the target sample at different locations of the target sample to obtain measurements of optical transmission of the target sample at the different locations as a result of the scanning. This scanning of the relative position between the target sample and the probe light can be a 2-dimensional scanning along directions transverse or perpendicular to the optical axis of the input optical module, e.g., x and y directions as shown in FIGS. 1 and 2 where the z axis is along the optical axis of the input optical module in some measurements. In other measurements, this scanning of the relative position between the target sample and the probe light can be a 3-dimensional scanning that includes the above 2D scanning and an additional scanning of an optical focus of the probe light at different focus positions along the optical axis of the input optical module (i.e., the z direction as shown in FIGS. 1 and 2). In either the 2D or 3D scanning, at each position in a scanning, one or more optical properties of the probe beam may be adjusted to obtain different measurements at each position, e.g., the optical wavelength of the probe light, or the optical polarization of the probe light.

The output optical module and the optical detector in FIGS. 1 and 2 are structured to collect the transmitted probe light from the target sample and to capture the 2D spatial distribution of the transmitted probe light at the optical detector at each scanning position in a 2D or 3D scan. The optical detector may be a 2D array of optical sensors or optical sensing pixels to capture the 2D spatial distribution of the transmitted probe light. In some measurements, the optical detection at the optical detector may be clocked to capture the temporal property of the transmitted probe light at the optical detector. The output of the optical detector that contains measurements of optical transmission of the target sample at the different locations is then processed by a processor to extract information on a structural pattern distribution or other property of the target sample.

Referring to the specific components used in the input and optical modules in FIGS. 1 and 2, an optical attenuator is included in the input optical module to adjust the optical power of the probe light for OTS measurements. This optical attenuator may be a tunable attenuator that produces different levels of attention and may be manually tuned or motorized as a step-wise variable attenuator, or a continuously variable optical element. The optical attenuator can reduce the power of radiation by a suitable mechanism, including, e.g., absorption, reflection, diffusion, scattering, deflection, diffraction, or dispersion.

The input and optical modules in FIGS. 1 and 2 are shown to include optical filters 1 and 2, respectively and are used to control the wavelength and the bandwidth of the probe light incident to the sample for inspection or the transmitted probe light as the registered radiation at the optical detector. Such an optical filter can be in various optical filter configurations, including, e.g., an optical absorptive filter, an optical interference filter, or a dichroic filter. The filter can be placed after the light source and/or in front of the detector.

The OTS system example in FIG. 1 includes optical polarizers 1 and 2 to control the polarization of the probe light output and registered radiation. Each polarizer can be tuned or rotated manually or using a motorized drive, and can be wire-grid, absorptive, beam-splitting, reflection, birefringent, thin film polarizers, etc. FIG. 2 further shows that a polarization state generator (PSG) and a polarization state analyzer (PSA) can be used to control the polarization of output and analyze registered radiation for SOP measurements. Polarization state generator and polarization state analyzer can be made with rotating wave plate and polarizer, or can be made with binary magneto-optic (MO) polarization rotators. Various optical polarization elements may be used in handling polarized light, e.g., a polarizing beam splitter in various configurations such as a polarizing beam cube or a birefringent polarizing beam device.

The diaphragms 1 and 2 are used to control the beam size. Such a diaphragm can be, for example, a pinhole or iris diaphragm and can be adjusted by using an automated control or be controlled manually.

In some implementations of the OTS system, variable focus lenses or telescopes 1 and 2 can be used to control the focus spot or beam divergence on the sample of the probe light from the input optical module or the beam divergence on the optical detector. A lens for this feature can be made of a glass, crystal or polymer material with a fixed or varying focus length (e.g., liquid polymer lens). For example, the focus of the input probe light at the sample can be adjusted along the z direction to focus the beam at different depths within the sample in 3D OTS measurements.

The optical detector can be a 2-dimensional array of optical detectors in many OTS measurements but may also be a single detector or a 1-dimensional array of optical detectors. Each optical detector is responsive to light to produce a detector signal that carries the information in the received light. A single detector or a 1-dimensional array of optical detectors as the optical detector may be used to obtain the 2-D spatial distribution of the transmitted probe light from the sample.

In implementations, the scanning of the relative position between the target sample and the probe light may be implemented by a scanner. For example, a scanner may be coupled to the light source and the optical detector to achieve the desired scanning. For another example, a scanner may be coupled to move the position of the sample to achieve the desired scanning. A scanner may be implemented as a 2D scanning stage or synchronized robotic arms.

In one of the OTS system used for tests, the light source was an iBeam-smart-640s laser diode with 640 nm fundamental wavelength, ~1.5 mm beam diameter that, and up to 150 mW output power. The transmitted radiation was received by using a DET36A Si detector with 350-1100 nm wavelength range, 14 ns rise time and 13 mm² active area. The voltage at the output of the photodetector was directly proportional to registered radiation power. The XY-coordinate stage with stepper motors allows for rapid raster scanning of the GFRP samples with a step size of 0.25 mm. The lateral resolution of OTS system was mainly determined by the beam diameter and was kept at 0.5 mm in the experiments.

The operation of an OTS system is based upon measuring the optical transmittance of a target material sample, e.g., a semi-transparent FRP composite, based on a relationship between the severity of damage and the level of transmitted radiation power measured with the photodetector. When the radiation in the probe light interacts with the material, various effects may occur, e.g., optical transmission, absorption, chromatic dispersion, diffraction, scattering, reflection, refraction, and optical conversion of the received probe light. The conversion of radiation occurs when the dielectric polarization of the medium responds nonlinearly to the applied electric field of the received probe light at the sample, and can be neglected if the medium is fairly linear. The optical refraction affects the direction of radiation propagation, and can be neglected if the incident radiation is normal to the interface. Diffraction is mostly prominent at the edges and is hardly manifested in the bulk of a material. Dispersion effects will be insignificant if the radiation is quasi-monochromatic. Note that these latter three effects influence the direction of radiation propagation rather than the energy or the power of radiation.

In FRP composites, optical power losses partially occur due to reflection, which happens whenever there is a mismatch between the refractive indexes of two materials (e.g., an interface such as a delamination). Optical reflection coefficients for s-polarized ($R_S$) and p-polarized ($R_P$) light at the interface between dielectric materials can be estimated by the following equations:

$$R_S = \left| \frac{n_1 \cdot \cos\theta_i - n_2 \cdot \sqrt{1 - \left(\frac{n_1}{n_2} \cdot \sin\theta_i\right)^2}}{n_1 \cdot \cos\theta_i + n_2 \cdot \sqrt{1 - \left(\frac{n_1}{n_2} \cdot \sin\theta_i\right)^2}} \right|, \quad (4)$$

$$R_P = \left| \frac{n_1 \cdot \sqrt{1 - \left(\frac{n_1}{n_2} \cdot \sin\theta_i\right)^2} - n_2 \cdot \cos\theta_i}{n_1 \cdot \sqrt{1 - \left(\frac{n_1}{n_2} \cdot \sin\theta_i\right)^2} + n_2 \cdot \cos\theta_i} \right|, \quad (5)$$

where $\theta_i$ is the angle of incidence, $n_1$ is the refractive index of the material through which the light is reflected; $n_2$ is the refractive index of the material through which light is further transmitted.

Equation 4 and Equation 5 hold for specular reflection from ideal mirror-like surfaces, and in the case of normal incidence ($\theta_i=0$) they reduce to the following formula:

$$R_{SP} = R_S = R_P = \left|\frac{n_1 - n_2}{n_1 + n_2}\right|^2 \quad (6)$$

For instance, at normal incidence angle, the specular reflection coefficient $R_{SP}$ for an air ($n_1=1$)/glass ($n_2 \approx 1.5$) interface is around 0.04, meaning that approximately 4% of incident radiation is reflected. However, if the surface is optically rough, such as an interface of interlaminar delamination, diffuse reflection can take place. A reflective surface with h some surface roughness may be modeled by a collection of small randomly disposed mirror-like facets. The reflection coefficient $R_d$ predicted by the model depended on specular reflection from these facets plus a diffuse component caused by multiple reflections and internal scattering:

$$R_d(\psi, \theta, \varphi) = \quad (7)$$

$$\frac{\delta N_{r,s}(\psi, \theta, \varphi) + \frac{\delta N_d(\psi)}{N_i(\psi) \cdot \cos\psi \cdot \delta\omega}}{} = \frac{\left[\frac{\left(b \cdot f \cdot N_i(\psi) \cdot \frac{\delta\omega}{4}\right) \cdot F(\psi', n') \cdot G(\psi_p, \theta_p)}{\cos\theta}\right] \cdot e^{-c^2 \cdot \alpha^2} + a \cdot N_i(\psi) \cdot \cos\psi}{N_i(\psi) \cdot \cos\psi \cdot \delta\omega},$$

where ψ is the zenith angle of incident radiation; θ and φ are the zenith and the azimuthal angles of reflected flux, respectively; $\delta N_{r,s}$ is the specular component of reflected flux;

$\delta N_{r,d}$ is the diffuse component of reflected flux; $N_i$ is the radiance of the small source; $\delta\omega$ is the solid angle of the source; F is the Fresnel reflectance; $\psi'$ is the angle of flux reflected from an elementary facet with a surface normal n'; G is a masking and shadowing factor; $\psi_p$ and $\theta_p$ are the projections of $\psi$ and $\theta$ onto the plane determined by the facet normal and the surface normal; $\alpha$ is the angle at which facet normals are inclined with respect to the normal of the mean surface; f is the area of an elementary facet; a, b and c are scalar constants that depend on surface preparation.

Equation 7 shows that the interaction of the radiation with the material is complex; and the reflection coefficient can change drastically depending on incident angle of radiation, observation angle, surface roughness, and refractive index. Since FRP composite refractive index itself depends on many factors, modeling of light propagation in composite material is a challenging and cumbersome task.

The analysis provided below offers guidance to the development of a simple and straightforward way to quantify the interior impact damage in materials, particularly laminated composites that have been subject to impacts.

If normally incident monochromatic and collimated laser radiation is passed along a local transect of a fairly linear and homogeneous medium without considering interfaces such as delaminations, the radiation transmitted to a downstream detector through such a medium can be approximately represented the following based on Equation 3:

$$P_{as} = P_0 \cdot (1-R_{ac}) \cdot T_{as} \cdot (1-R_{ca}), \quad (8)$$

where $R_{ac}$ and $R_{ca}$ are the reflection coefficients of air-to-composite and composite-to-air interfaces, respectively.

Changes in registered power $P_{as}$ defined by Equation 8 can be explained by local variations of fiber/matrix content and thickness over the extent of a composite test specimen in its pristine condition. This conclusion follows from Equation 3, assuming that the reflection coefficients at the top and bottom surfaces, $R_{ac}$ and $R_{ca}$ remain constant.

An extension of Equation 8 can be used to determine the power of the transmitted radiation $P_T$ in the presence of defects such as delaminations by including reflections at interlaminar interfaces:

$$P_T = P_{as} \cdot (1-R_1) \cdot (1-R_2) \cdot \ldots \cdot (1-R_N) = P_{as} \cdot T_{R1} \cdot T_{R2} \cdot \ldots \cdot T_{RN}, \quad (9)$$

where $R_1, R_2, \ldots R_N$ and $T_{R1}, T_{R2}, \ldots T_{RN}$ are the local reflection and transmission coefficients for each of the N delaminations in the transect of the sample, respectively. Each reflection or transmission coefficient takes into account the combined losses at both composite-to-air and air-to-composite interfaces of a delamination, e.g., $T_{R1} = T_{R1}^{ca} \cdot T_{R1}^{ac} = (1-R_{R1}^{ca}) \cdot (1-R_{R1}^{ac})$.

Actual calculation of $P_T$ using Equation 9 is problematical because a map of delaminations with their respective transmission coefficients, $T_{R1}, T_{R2}, \ldots T_{RN}$, is not known a priori. A practical solution is to replace the set of unknown transmission coefficients by a single "standard" value T:

$$P_T \sim P_{as} \cdot T^N, \quad (10)$$

The transmission coefficient T is determined by scanning a representative sample containing a single interior delamination. Hence, if delamination is considered to be the main damage mechanism, then Equation 10 can be used to relate the registered transmitted power and the number of delaminations.

Determination of a "Standard" Transmission Coefficient T

In conducted tests, the value of T was obtained from the OT-scan of a double cantilever beam (DCB) sample after the mode I interlaminar fracture toughness test (per the ASTM D5528 standard). The DCB sample used in tests included eight layers of plain-weave S2 glass with a single fracture-induced delamination between the four upper and four lower laminates. The OT-scan was acquired with a laser output power of 5.2 mW and a lateral resolution of 0.5 mm. The transmission coefficient was calculated as the ratio of the transmitted radiation powers $P_T$ and $P_{as}$ averaged over two separate 2 cm² regions of the sample, one region containing the crack and the other without a crack as shown in FIGS. 3 and 4. The sample was clamped with a few miniature C-clamps prior to OTS to ensure that the crack was closed as tightly as possible. The value of T was found to be 0.61, apparently owing to the diffuse surface of the crack interface.

Robustness of OTS

The power calculations in Equation 8 and Equation 9 are for characterizing only ballistic photons in the transmitted probe light through a sample and such ballistic photons travel from a point-like radiation source down to the photodetector in a straight line. If a collimated beam with a large diameter propagates through a scattering medium such as a GFRP, the transmitted radiation can include contributions from scattered photons, taking on some sort of an angular distribution in their scattering paths. In such a case, the size of the delamination/air gap inside the sample, variation of sample thickness, and the distance between the detector and the output interface might affect the measurement of the transmitted radiation. In addition, propagation of a wide laser beam through the edges of delaminations can introduce partial attenuation and, possibly, edge diffraction effects. These issues can be addressed by using a laser with a small beam diameter, or by installing a diaphragm with a pin hole in front of the detector.

In the sample OTS system for conducting the tests, the effect of a relatively large beam footprint (d~1.5 mm) was compensated for in signal processing, which allowed for more accurate detection of delamination boundaries. The uncertainties in the determinations of the delamination contours were mainly governed by the size of the footprint of the laser beam and the associated transition region rather than by uncertainties in the estimation of T, as will be seen in the next section.

The disclosed OTS system has a self-referencing capability. As shown by Equation 10, the thickness of the composite sample and the delamination depth do not affect the transmission coefficient for a single interface (delamination) T, because it is defined as the ratio of the radiation $P_T$ transmitted through the region with the delamination to the radiation $P_{as}$ transmitted through the healthy region of the sample.

Data Analysis and Imaging Algorithm

FIGS. 3A and 3B show images of GFRP samples without being subject to impact and after being subject to impact. The first GFRP sample on the left in FIG. 3A was healthy without defects (no impact), and the second GFRP sample on the right in FIG. 3B was damaged by the impact under a low velocity impact of 20 J.

OTS tests were conducted on the two GFRP samples by using a laser output power of 5.2 mW and a spatial resolution of 0.5 mm. The distance between the bottom side of the sample and the receiver was 5 mm. The raw results before post-processing are demonstrated in FIGS. 4A and 4B. As seen from FIG. 4A, some areas of the plain weave GFRP plate with no damage had higher transmittance than other areas, which was apparently caused by thickness variations of the sample and glass fiber irregularities as follows from Equation 3. The transmitted power $P_{as}$ was minimal when radiation propagated via clusters of fibers. In contrast, the highest $P_{as}$ corresponded to propagation of radiation via resin-rich areas. Hence, in the case of the pristine GFRP composite, the amplitude values in the output of the photodetector fell in a region $\Gamma_0 = [A_{max}, A_{min}]$ which was directly proportional to the range of transmitted powers $[P_{as}^{max}, P_{as}^{min}]$.

The incident power from the laser source, $P_0$ was adjusted before each scan such that the maximum amplitude registered by the photodetector $A_{max}$ was as close as possible to its saturation limit of 10 V in order to provide the widest measurement range and the highest SNR.

Owing to the mismatch of material properties at the interfaces within the GFRP composite plate, the low velocity impact with E=20 J resulted in multiple interlaminar delaminations whose areas increased with depth. In order to quantify the extent and severity of impact damage from the OTS scans, an advanced signal processing procedure can be provided to determine the delamination contours as a function of depth. This procedure includes estimating threshold levels for determining maximal and minimal amplitudes of transmitted photons of a histogram of defect-free regions in the target sample and computing contour margins of delaminations in the target sample based on an optical transmission property of a reference sample that has a single delamination.

This signal processing procedure is illustrated in FIGS. 5A through 5D. Assuming that delamination is the main damage mechanism, the registered power of radiation transmitted through the sample $P_T$ can be divided into discrete amplitude levels depending on the number of interfaces below the scan point that affect the beam power. If the transmission coefficient T of a similar FRP sample with one delamination in its mid-plane is known and only diffuse reflection is assumed, meaning no increase in scattering or absorption is taken into account, the range $[A_{max}, A_{min}]$ associated with the pristine composite can be simply scaled down to plot damage contours representing N delaminations. The scaling factor can be established through the use of Equation 10 as:

$$\Gamma_N = \Gamma_0 \cdot T^N = [A_{max}, A_{min}] \cdot T^N \qquad (11)$$

Figures 5A, 5B, 5C, 5D:
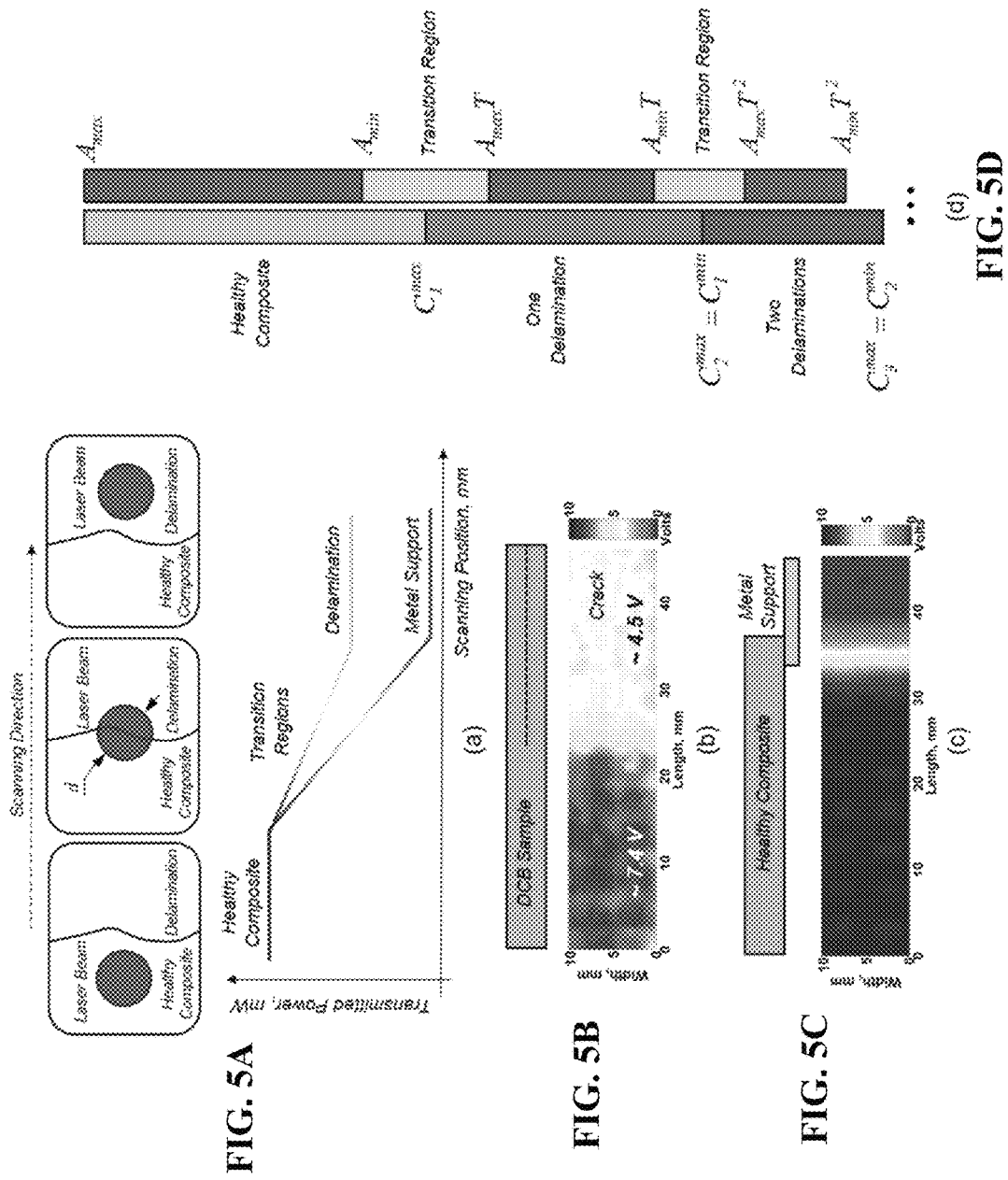
FIG. 5A shows a change of transmitted radiation power across delamination boundary due to partial beam scattering through the transition regions.
FIG. 5B shows an OT-scan of the double cantilever beam (DCB) sample with a crack that served as the "standard".
FIG. 5C shows an OT-scan of the metal-to-composite interface in the support region.
FIG. 5D shows a determination of contour levels corresponding to different numbers of delaminations.

As suggested above, it is assumed that each delamination encountered has a transmission coefficient T that is reasonably near the value found for the single delamination in the "standard" specimen. However, in some cases, the intensity values may not fall in any of these discrete intervals. This happens because the incident laser beam is not focused and has a footprint of d~1.5 mm. It was observed that at the boundaries between each delamination and the sample there were smooth transition regions that were caused by partial attenuation of the incident beam. FIG. 5A through 5C illustrate this behavior conceptually for regions near the delamination in the "standard" specimen (FIG. 5B) and near the specimen supporting structure (FIG. 5C). The widths of the transition regions were estimated to be 2·d~3 mm. So, the intermediate values were arbitrarily split equally between the adjacent levels, and the new contour margins were computed as illustrated in FIG. 5D to be:

$$C_N^{max} = \frac{(A_{max} \cdot T + A_{min}) \cdot T^{N-1}}{2}, \qquad (12)$$

-continued $$C_N^{min} = \frac{(A_{max} \cdot T + A_{min}) \cdot T^N}{2}, \qquad (13)$$

where $C_N^{max}$ and $C_N^{min}$ are the upper and lower levels of contours corresponding to the $N^{th}$ delamination, $A_{max}$ and $A_{min}$ are the maximal and minimal amplitudes of registered radiation transmitted through a healthy composite, taken as the amplitudes of the corresponding detector output voltages, and T is the transmission coefficient of the "standard" sample with a single delamination in its mid-plane.

Figure 6B:
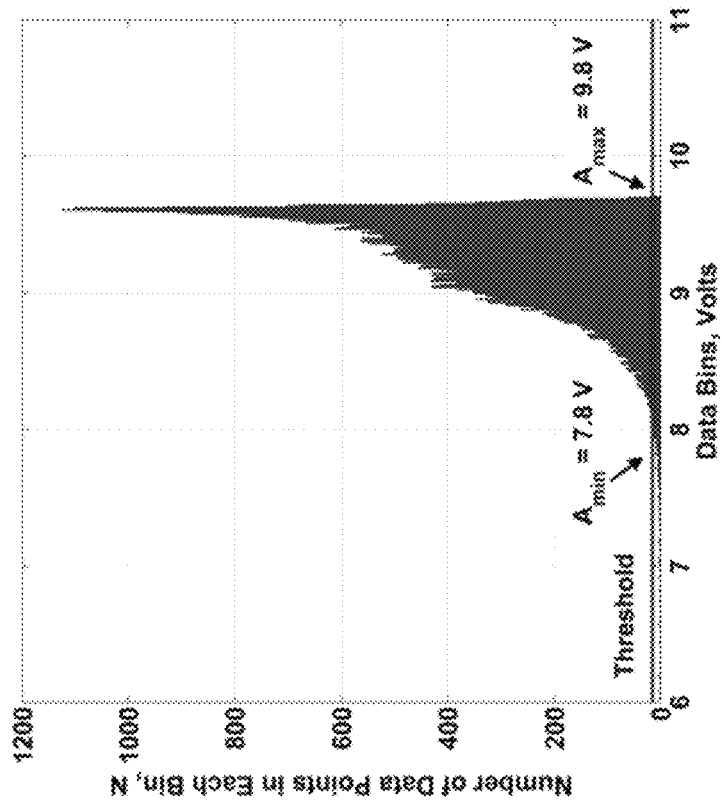
FIG. 6B shows a histogram of the corresponding region and threshold levels for determining maximal and minimal amplitudes of transmitted radiation $A_{max}$ and $A_{min}$.
Figure 6A:
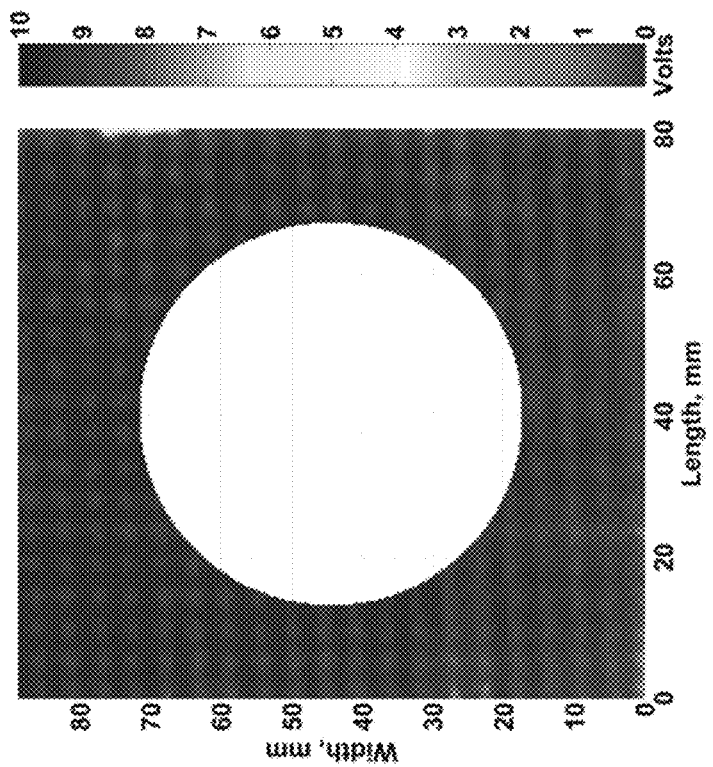
FIG. 6A shows an OT-scan of the GFRP sample after E=20 J impact, using only the healthy region without damage for estimating $A_{max}$ and $A_{min}$

The values of $A_{max}$ and $A_{min}$ were computed for healthy and impacted GFRP samples by considering the histograms of their healthy regions only (see FIG. 6A). The voltage outputs of the photodetector were split into 512 bins, whose mean values were sorted in ascending order. The $A_{min}$ was selected as the average of the first bin containing more than 25 elements. Similarly, the $A_{max}$ was assigned the average of the last bin, whose number of elements exceeded the same threshold. This procedure was applied to remove measurement variations potentially caused by the circuit noise, tilt of the sample, surface roughness or contamination, and vibration of the fixture during the acquisition of the OT-scans.

Figures 7A, 7B:
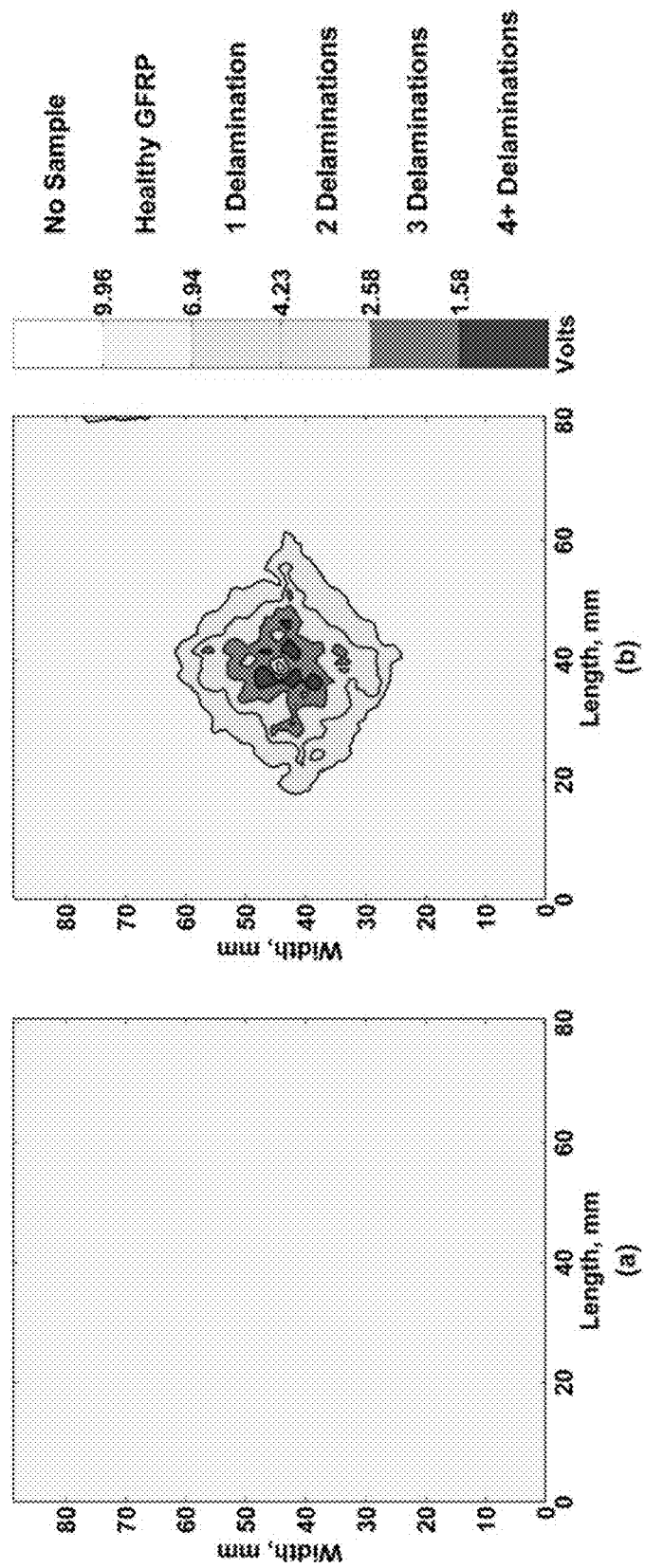
FIG. 7A shows a post-processed OT-scan of the healthy sample.
FIG. 7B shows a post-processed OT-scan of the sample after E=20 J impact.

Post-processed OTS data of healthy and impacted GFRP samples are shown in FIG. 7A AND 7B. The color bar of contour plots was partitioned as per Equations 12 and 13 to highlight the healthy regions of each composite plate and the regions with given numbers of delaminations. As seen from FIG. 6B, the total delamination count was the largest in the middle region of the impacted sample, and it decreased radially from the point of impact. In addition, the extents of delaminations were slightly larger along the principle directions of the glass fibers, $[0/90]_4$. The results demonstrated that it was difficult to determine the differences between contours for a large number of interlaminar defects, in particular, for N>4, because the margins became too closely spaced and the overall level of radiation intensity at the photodetector approached the noise limit. Hence, whenever the voltage output of the photodetector fell below $C_4^{min} = 1.58$ V, this indicated that N exceeded four, which is simply denoted as "4+" in the subsequent figures.

OTS Validation

Figures 8A, 8B, 8C, 8D, 8E, 8F:
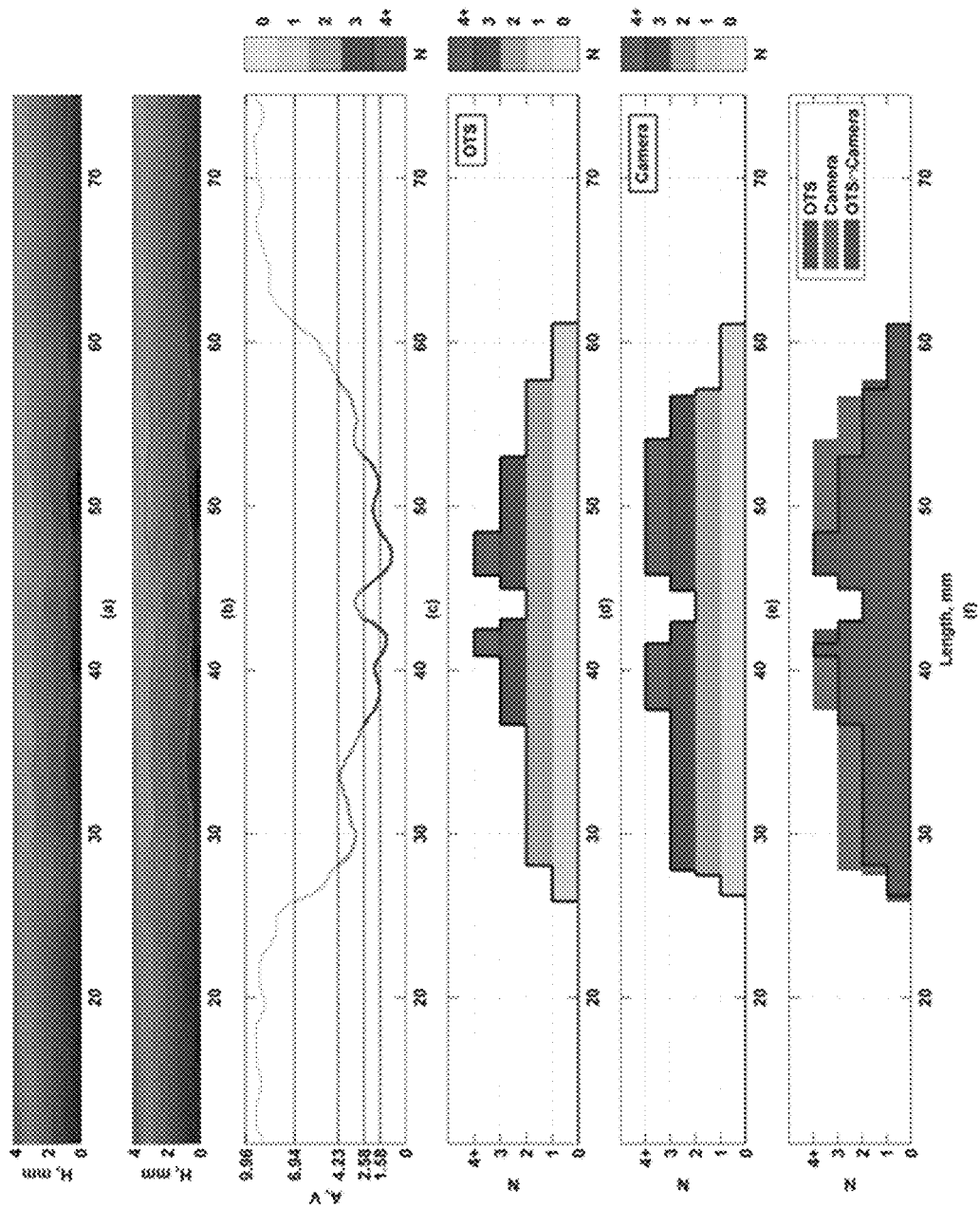
FIG. 8A shows a cross-section of the GFRP sample (thickness H=4.8 mm, impact energy E=20 J).
FIG. 8B shows delaminations identified using edge detection and filtering of the image data.
FIG. 8C shows a corresponding OT-linescan.
FIG. 8D shows the number of delaminations, N registered by the OTS.
FIG. 8E shows the number of delaminations, N along the cross-section length obtained from post-processed digital camera images.
FIG. 8F shows a comparison of results obtained with OTS and digital camera imaging wherein the regions in which the numbers of detected delaminations match are highlighted in purple.

The impacted sample (E=20 J) shown in FIG. 3B was cut with a diamond saw at location x=37.8 mm along its y-axis (see the corresponding OT-scan in FIG. 4b). The left half of the sample was arbitrarily chosen for determining the delamination contours. Its new face created after cutting was saturated with a UV dye penetrant, and it was left to soak for 30 minutes. After absorption of the UV dye by the interlaminar defects, the sample was illuminated with a UV lamp in a dark ambience in order to enhance the contrast between the delaminations and the pristine GFRP material in the transect. The image of the cross-section was taken with a digital camera, and it was later converted into a gray-scale format for post-processing in MATLAB with the result shown in FIG. 8A. Delaminations were identified using the two-stage Canny edge detection algorithm followed by Wiener filtering to smooth the image and remove the residual artifacts. Applying a hard threshold to the resulting image effectively converted it into a binary representation, whose high-value pixels determined the delamination boundaries, and whose zero-value pixels corresponded to the pristine GFRP material. FIG. 8B shows the obtained binary image merged with the original digital picture of the cross-section area. The delaminations were highlighted as red curves, and the total number of delaminations at a given scanning position was easily determined by automatically counting the number of curves through the height of the image.

FIG. 8C illustrates the OT-linescan of the corresponding cross section of the GFRP sample. In this figure, the curve is partitioned based on the voltage levels determined from Equation 12 and Equation 13. Thereby, if the total number of delaminations N in the cross-section changes, this is highlighted with a different color in accordance with the discrete color map on the right hand side.

The total number of delaminations along the cross-section of the GFRP sample, determined from the OT-linescan and the post-processed digital image, are shown in FIG. 8D and FIG. 8E, respectively. Both plots are well aligned along the x-axis, which indicates that the OTS technique accurately determines the outer margins of the impact damage. In addition, one of the characteristic features of the scanned sample is that only two delaminations appear in the middle of the cross-section, as seen from the FIG. 8B. This trend is very well captured by the OTS system. In FIG. 8F both results are plotted on top of each other, and the regions in which the numbers of delaminations detected by the two methods match are highlighted in purple. As seen, the results obtained with OTS and the digital camera match well, differing at most by one delamination. This difference can be explained by the fairly large transition region of the laser beam (2·d≈3 mm) and light scattering previously discussed. At the same time, the digital image of the cross section shows the distribution of the impact damage only in two dimensions. However, the damage is three-dimensional, and if the number of delaminations in the plane parallel to the transect of the sample is not constant within the footprint of the laser beam, the amount of the received radiation at the downstream photodetector would be affected.

Selected Technical Features of Disclosed OTS

1. Fast Scanning Using Line and Plane Light Sources

In some implementations of the disclosed OTS, the point light source of the above-described OTS setup can be replaced with a line shaped light source (e.g., with slit aperture, light source array, or scanning beam) or a plane-shaped light source in combination with suitable 1D or 2D detector. Hence, this modification allows much faster inspection by replacing raster scan with 1D scan or instant snapshot.

2. Discrimination of Scattered and Ballistic Photons

Discrimination of scattered photons from the ballistic photons can be important in applications, where scattering properties of studied material are evaluated. The above described OTS setup can be modified in a way that ballistic and scattered photons can be discriminated. The separation of scattered photons from the ballistic ones can be achieved through multiple ways.

One way is to use a pinhole or 2D detector to spatially discriminate ballistic photons from the scattered photons. In this case, only ballistic photons will be registered in the center of the detector; and the portion of scattered photons can be easily calculated by subtraction of radiation power of the ballistic photons from the total radiation power.

Figure 9:
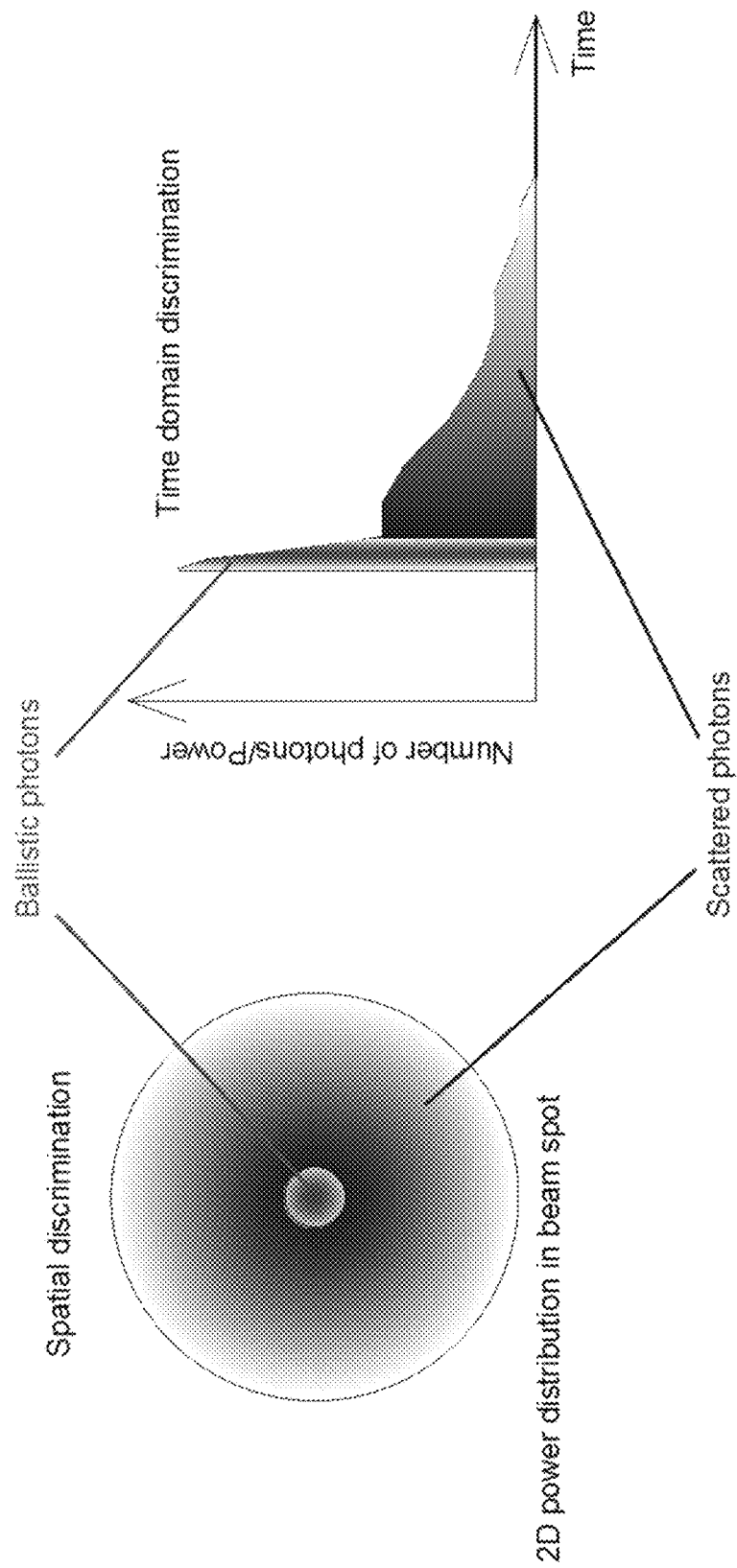
FIG. 9 shows two examples of optical detection techniques for separating measurements of optical transmission by ballistic photons and scattered photons in the transmitted probe light from a sample.

Another way is to separate the photons in time domain using a high-speed optical detector. In this case, ballistic photons will contribute to the registered signal with characteristic spike, while scattered radiation will have broad envelope following the peak from ballistic photons. Both spatial and time domain discrimination techniques are illustrated in FIG. 9.

Additionally, since the light scattering, e.g., Rayleigh scattering, depends on the inspection wavelength, the light source array or tunable light source also provides the ability to discriminate scattered from ballistic photons. If absorption spectrum of the studied material is known, and Rayleigh scattering proportional to $\lambda^{-4}$ is taken into account, transmitted radiation for two inspection wavelengths $\lambda_1$ and $\lambda_2$ can be approximated as:

$$\begin{cases} P_1 \approx (1 - A_1) \cdot \left(B + \dfrac{S}{\lambda_1^4}\right) \\ P_2 \approx (1 - A_2) \cdot \left(B + \dfrac{S}{\lambda_2^4}\right) \end{cases} \quad (14)$$

where $A_1$ and $A_2$ are known absorption constants, B is the portion of ballistic photons, and S is proportional to the number of scattered photons. The solution to Equation 14 yields:

$$B \approx \frac{1}{(\lambda_1^4 - \lambda_2^4)} \cdot \left[\frac{P_1 \cdot \lambda_1^4}{1 - A_1} - \frac{P_2 \cdot \lambda_2^4}{1 - A_2}\right] \quad (15)$$

3. 3D Scanning

In order to obtain three dimensional location of the defect inside the material, a 3D scanning can be implemented. Some implementations of the disclosed OTS can be used to identify the depth of the defect along with in-plane defect position. One way to perform such scanning is to analyze the transmitted power dependence on focal plane position. In this case the focus is shifted manually or by an automated mechanism, e.g., using variable focus lens from the front to the rear surface of the studied sample.

Figure 10A:
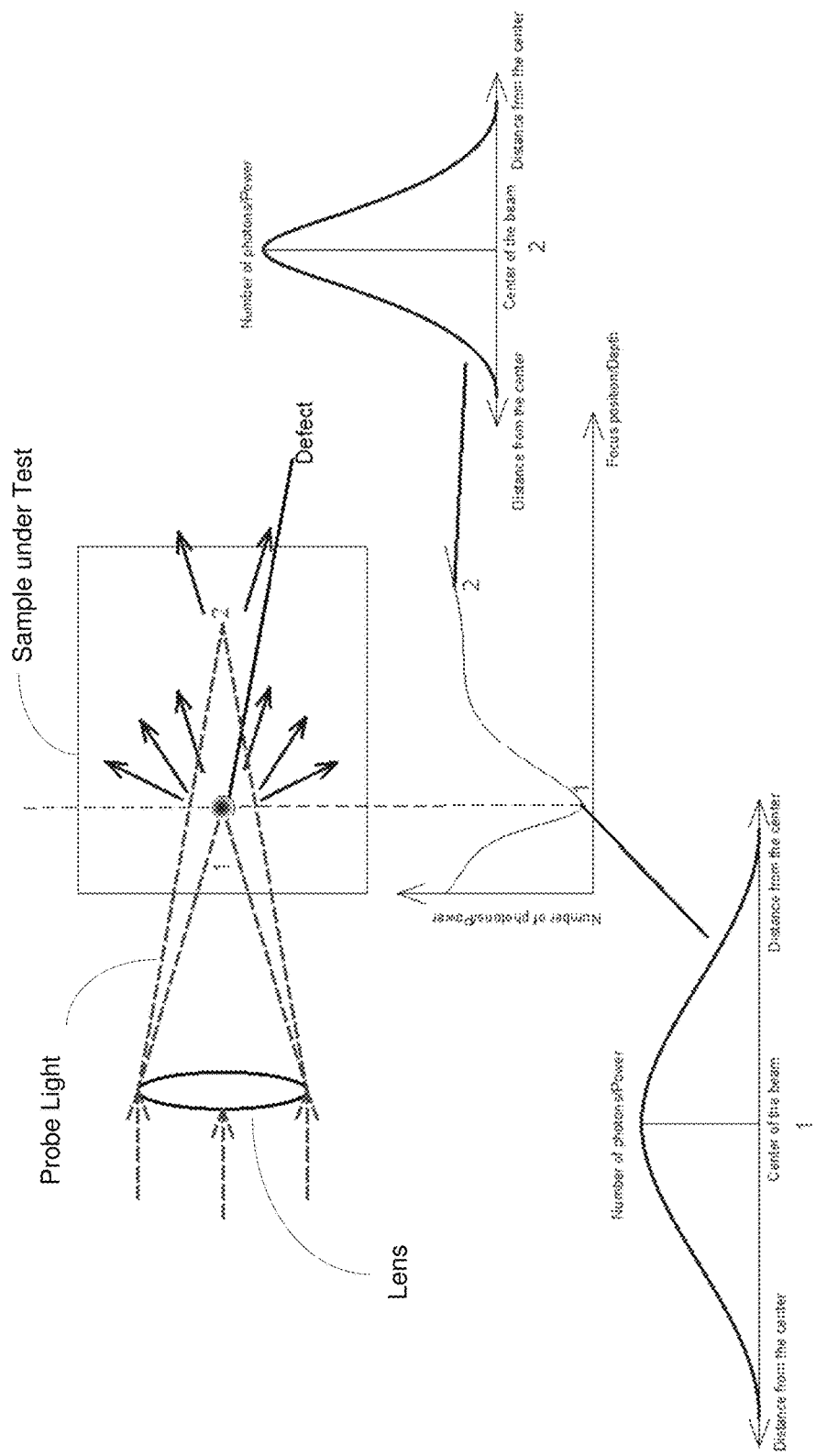
FIG. 10A illustrates an example of scattering defect inside the sample.

FIG. 10A illustrates an example of scattering defect inside the sample. When the focus position is in the vicinity of the defect (position 1), majority of the radiation will be scattered by the former causing maximum scattering and local minimum in the registered power. In case of focal position 2 only small portion of the incident radiation is scattered by the defect, hence the registered power will be higher compared with previous case.

Figure 10B:
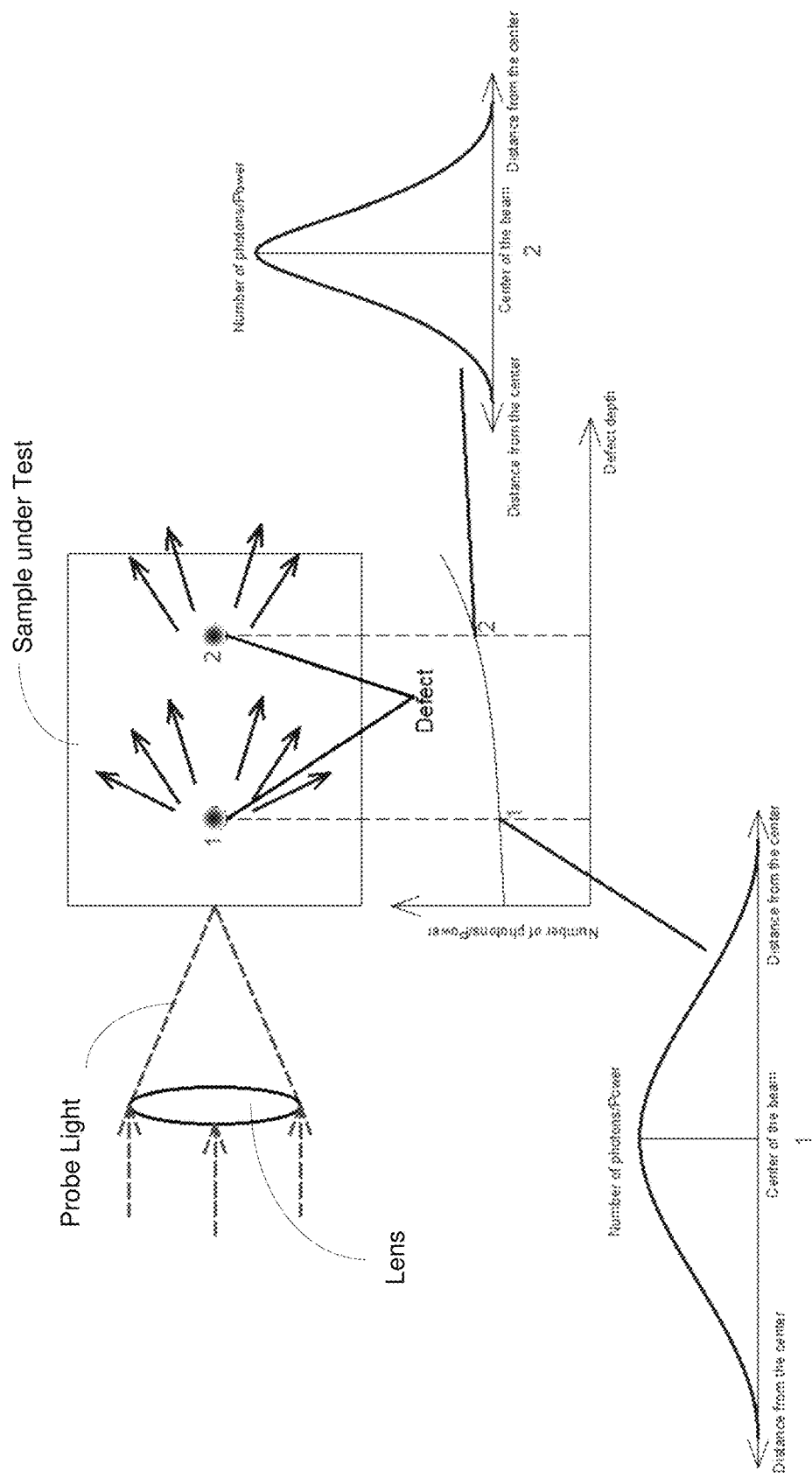
FIG. 10B shows an example with a defect in position 1 which occurs before a defect in position 2.

Another way is to correlate 2D scattering pattern on the defect depth. In this case the focus is fixed at optimal position; and power distribution is studied using 2D detector. In example shown in FIG. 10B defect with position 1 occurs before defect with position 2. This causes more radiation to be scattered from the center resulting in lower registered radiation and altered power distribution at the detector (less energy is concentrated in the inner area of the beam).

4. Optical Retardation Measurement

Some OTS implementations can use the polarizer configuration in OTS to obtain optical retardation of the material, which can be used to visualize internal stresses. The setup is identical to photoelasticity setup, where polarizer 1 and 2 can be a linear polarizer or combination of is a combination linear polarizer and ¼λ, wave plate. The configuration of polarizers can be orthogonal to each other, i.e., dark field, or parallel to each other, i.e., light field. Referring back to FIG. 2, A PSG can be implemented in the input optical module on the OTS system and a PSA can be implmente din the output optical module for measuring the changes in state of polarization caused by the material under test. Such SOP measurements can be used to visualize internal stresses and structure.

Figure 11A:
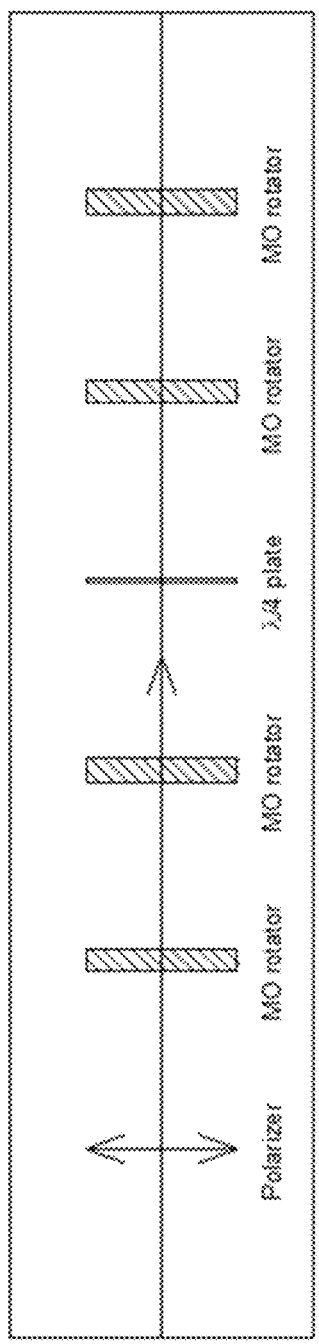
FIG. 11A illustrates an example of a polarization state generator (PSG).
Figure 11B:
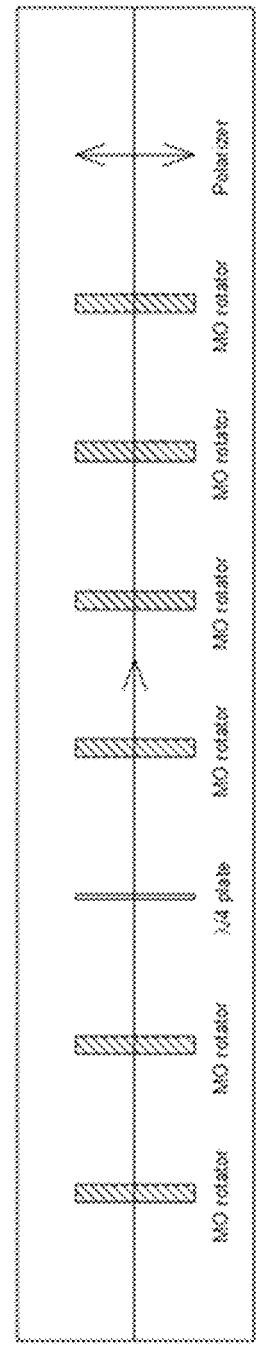
FIG. 11B illustrates an example of a polarization state analyzer (PSA).

Examples of PSG and PSA are shown in FIGS. 11A and 11B, respectively. MO rotator has the following attractive properties: when a positive magnetic field is applied above a saturation field, the rotator rotates the SOP by a precise angle near 22.5°. When a negative magnetic field is applied beyond saturation, the rotator rotates the SOP by a precise angle near −22.5°. Therefore, when both rotators in each pair rotate in the same direction, the net rotation is +45° or −45°. If the two rotators rotate in opposite directions, however, the net SOP rotation is zero. Assuming that the polarizer is aligned with the c axis of the λ/4 plate, the following SOPs can be generated by PSG (referenced with respect to the polarizer direction):

a. A linear SOP at 0° when the rotators in both pairs rotate in opposite directions.
b. A linear SOP at +45° when the rotators in the first pair rotate in opposite directions but the rotators in the second pair both rotate +22.5°.
c. A linear SOP at −45°, when the rotators in the first pair rotate in opposite directions but the rotators in the second pair both rotate −22.5°.
d. RHC, when the rotators in the first pair both rotate 22.5°.
e. LHC, when the rotators in the first pair both rotate −22.5°.

Three are 16 SOP combinations of 4 bits; however, only five states are distinctive and the rest are degenerate. For Mueller matrix calculations, only four distinctive SOPs are required. However, some applications may require six distinctive SOPs for better calibration accuracy. To generate six such polarization states another MO rotator pair is added to the device (after the second pair) to produce additional +45° and −45° rotations, similarly to PSA shown in FIG. 2. Note that this 6-bit device (with six binary MO switches) can theoretically generate 64 states; however, only six states are nondegenerate Mueller matrix M of inspected sample can be obtained using combination of PSG and PSA shown in FIGS. 2 and 11. Let the Stokes vector of the ith output of the PSG be:

$$S_i^{PSG} = \begin{pmatrix} S_{0i}^{PSG} \\ S_{1i}^{PSG} \\ S_{2i}^{PSG} \\ S_{3i}^{PSG} \end{pmatrix}$$

The corresponding Stokes vectors measured by the PSA after the light passes through the sample are related to Mueller Matrix M by:

$$S_i^{PSA} = \begin{pmatrix} S_{0i}^{PSA} \\ S_{1i}^{PSA} \\ S_{2i}^{PSA} \\ S_{3i}^{PSA} \end{pmatrix} = \begin{pmatrix} m_{00} & m_{01} & m_{02} & m_{03} \\ m_{10} & m_{11} & m_{12} & m_{13} \\ m_{20} & m_{21} & m_{22} & m_{23} \\ m_{30} & m_{31} & m_{32} & m_{33} \end{pmatrix} \begin{pmatrix} S_{0i}^{PSG} \\ S_{1i}^{PSG} \\ S_{2i}^{PSG} \\ S_{3i}^{PSG} \end{pmatrix}$$

At least 4 non-degenerate SOPs must be generated by the PSG and analyzed by the PSA to completely determine Mueller Matrix M by solving Equation 26. In such a case, i=0, 1, 2, 3 in Equation 25 and Equation 26. However, for higher accuracies, we require that as many as 6 nondegenerate SOPs be generated by the PSG and analyzed by the PSA, so that i=0, 1, 2 . . . 5. Define a new matrix $S^{PSA}$ as:

$$S^{PSA} = \begin{pmatrix} S_{00}^{PSA} & S_{01}^{PSA} & S_{02}^{PSA} & S_{03}^{PSA} & S_{04}^{PSA} & S_{05}^{PSA} \\ S_{10}^{PSA} & S_{11}^{PSA} & S_{12}^{PSA} & S_{13}^{PSA} & S_{14}^{PSA} & S_{15}^{PSA} \\ S_{20}^{PSA} & S_{21}^{PSA} & S_{22}^{PSA} & S_{23}^{PSA} & S_{24}^{PSA} & S_{25}^{PSA} \\ S_{30}^{PSA} & S_{31}^{PSA} & S_{32}^{PSA} & S_{33}^{PSA} & S_{34}^{PSA} & S_{35}^{PSA} \end{pmatrix}$$

$$= \begin{pmatrix} m_{00} & m_{01} & m_{02} & m_{03} \\ m_{10} & m_{11} & m_{12} & m_{13} \\ m_{20} & m_{21} & m_{22} & m_{23} \\ m_{30} & m_{31} & m_{32} & m_{33} \end{pmatrix} \begin{pmatrix} S_{00}^{PSA} & S_{01}^{PSA} & S_{02}^{PSA} & S_{03}^{PSA} & S_{04}^{PSA} & S_{05}^{PSA} \\ S_{10}^{PSA} & S_{11}^{PSA} & S_{12}^{PSA} & S_{13}^{PSA} & S_{14}^{PSA} & S_{15}^{PSA} \\ S_{20}^{PSA} & S_{21}^{PSA} & S_{22}^{PSA} & S_{23}^{PSA} & S_{24}^{PSA} & S_{25}^{PSA} \\ S_{30}^{PSA} & S_{31}^{PSA} & S_{32}^{PSA} & S_{33}^{PSA} & S_{34}^{PSA} & S_{35}^{PSA} \end{pmatrix}$$

$$= M \cdot S^{PSG}$$

Consequently, the Mueller matrix M of the inspected sample can be obtained from [:

$$M = S^{PSA} \cdot (S^{PSG})^T \cdot [S^{PSG} \cdot (S^{PSG})^T]^{-1},$$

where $(S^{PSG})^T$ is the transpose of matrix $S^{PSG}$.

The changes in SOP parameters may be attributed to the superstructure, defects, or introduced stresses inside the tested sample.

5. Algorithm for Obtaining the Number of Defects Inside the FRP Composites

Some OTS implementations can apply an algorithm for quantitative damage analysis in FRP composites using OTS system as presented below. The physical principle of the algorithm is described in connection with Equations 8-10 in the previous sections.

6. Multi-Wavelength Evaluation of Studied Material

The OTS setup can be configured to produce probe light at different inspection wavelengths. Since the attenuation properties depend on the inspection wavelength, the use of multiple wavelengths for inspection, e.g., light source array or tunable light source, allows more detailed evaluation of studied materials. For example, different defects may be more pronounced and "visible" for one or more particular wavelengths. This use of probe light at different optical wavelengths can be implemented to evaluate complex structures with two or more materials, such as lap-joints. Method for evaluation of adhesive lap-joint is provided below as an example.

Figure 12:
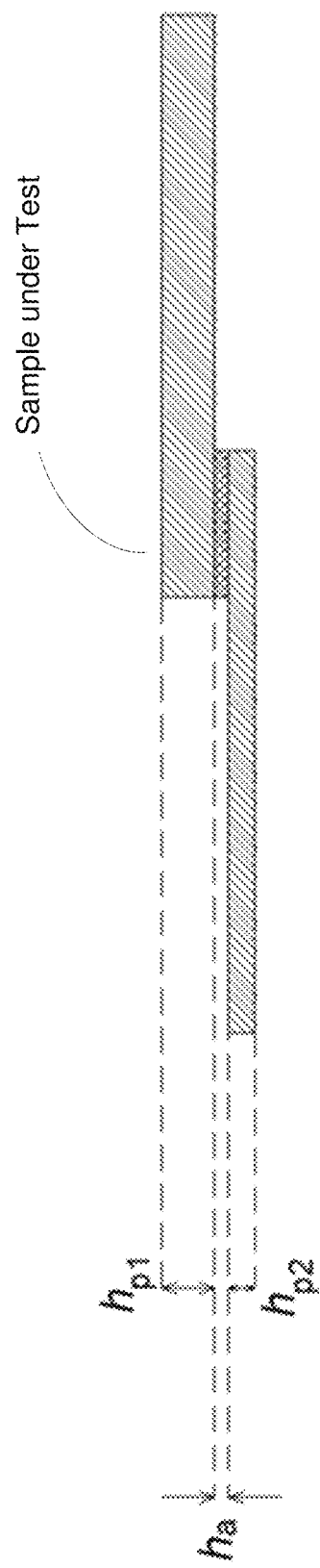
FIG. 12 illustrates an example of multi-wavelength evaluation of complex structures.

For example, plates and adhesives in a material may be considered homogeneous, hence, Equation 3 can be used to evaluate the transmittance properties at every XY coordinate. FIG. 12. illustrates the adhesive lap-joint comprised of two plates with adhesive layer in between. Combined plates thickness is $h_p = h_{p1} + h_{p2}$ and adhesive layer thickness is $h_a$.

According to Equation 3, the transmitted power $P_i$ for i-th inspection wavelength will be:

$$P_i = P_0 \cdot e^{-(\alpha_{pi} \cdot h_{p1} + \alpha_{ai} \cdot h_a + \alpha_{pi} \cdot h_{p2})} = P_0 \cdot e^{-(\alpha_{pi} \cdot h_p + \alpha_{ai} \cdot h_a)}$$

where $P_0$ (known) is the power of incident radiation and $\alpha_{pi}$ and $\alpha_{ai}$ are known attenuation coefficients for i-th inspection wavelength of homogeneous plate and adhesive, respectively. Thus, every Equation 14 contains the same two unknowns, $h_p$ and $h_a$. In order to solve it for homogeneous materials, one needs two inspection wavelengths. If plate and adhesive are not homogeneous, i.e., $\alpha_{pi} = \alpha_{pi0} + \alpha_{pi}'$ and $\alpha_{ai} = \alpha_{ai0} + \alpha_{ai}'$, where $\alpha'_{pi}$ and $\alpha'_{ai}$ are local perturbations of attenuation properties $\alpha_{pi0}$ and $\alpha_{ai0}$ of plate and adhesive, respectively, every Equation 14 will contain four unknowns.

In this case four and more inspection wavelengths might be required to fit the equations and estimate the thicknesses and local attenuation coefficients of plates and adhesive.

In case of homogeneous materials if two wavelengths are used for inspection, the following process can be performed for extracting structural information based on OTS measurements at two different optical wavelengths:

$$\begin{cases} P_1 = P_0 \cdot e^{-(\alpha_{p1}h_p + \alpha_{a1}h_a)} \\ P_2 = P_0 \cdot e^{-(\alpha_{p2}h_p + \alpha_{a2}h_a)} \end{cases}$$

$$\begin{cases} \ln\left(\frac{P_0}{P_1}\right) = \alpha_{p1} \cdot h_p + \alpha_{a1} \cdot h_a \\ \ln\left(\frac{P_0}{P_2}\right) = \alpha_{p2} \cdot h_p + \alpha_{a2} \cdot h_a \end{cases}$$

$$\begin{cases} \ln\left(\frac{P_0}{P_1}\right) = \alpha_{p2} - \ln\left(\frac{P_0}{P_2}\right) \cdot \alpha_{p1} = \alpha_{a1} \cdot \alpha_{p2} \cdot h_a - \alpha_{a2} \cdot \alpha_{p1} \cdot h_a \\ \ln\left(\frac{P_0}{P_1}\right) = \alpha_{a2} - \ln\left(\frac{P_0}{P_2}\right) \cdot \alpha_{a1} = \alpha_{a2} \cdot \alpha_{p1} \cdot h_p - \alpha_{a1} \cdot \alpha_{p2} \cdot h_p \end{cases}$$

$$\begin{cases} h_a \cdot (\alpha_{a1} \cdot \alpha_{p2} - \alpha_{a2} \cdot \alpha_{p1}) = \ln\left(\frac{P_0}{P_1}\right)^{\alpha_{p2}} - \ln\left(\frac{P_0}{P_2}\right)^{\alpha_{p1}} \\ -h_p \cdot (\alpha_{a1} \cdot \alpha_{p2} - \alpha_{a2} \cdot \alpha_{p1}) = \ln\left(\frac{P_0}{P_1}\right)^{\alpha_{a2}} - \ln\left(\frac{P_0}{P_2}\right)^{\alpha_{a1}} \end{cases}$$

$$\begin{cases} h_a \cdot (\alpha_{a1} \cdot \alpha_{p2} - \alpha_{a2} \cdot \alpha_{p1}) = \ln\left[\frac{\left(\frac{P_0}{P_1}\right)^{\alpha_{p2}}}{\left(\frac{P_0}{P_2}\right)^{\alpha_{p1}}}\right] \\ h_p \cdot (\alpha_{a1} \cdot \alpha_{p2} - \alpha_{a2} \cdot \alpha_{p1}) = \ln\left[\frac{\left(\frac{P_0}{P_2}\right)^{\alpha_{a1}}}{\left(\frac{P_0}{P_1}\right)^{\alpha_{a2}}}\right] \end{cases}$$

$$\begin{cases} h_a \cdot (\alpha_{a1} \cdot \alpha_{p2} - \alpha_{a2} \cdot a_{p1}) = \ln\left[\frac{P_0^{(\alpha_{p2}-\alpha_{p1})}}{P_1^{\alpha_{p2}} \cdot P_2^{-\alpha_{p1}}}\right] \\ h_p \cdot (\alpha_{a1} \cdot \alpha_{p2} - \alpha_{a2} \cdot a_{p1}) = \ln\left[\frac{P_0^{(\alpha_{a1}-\alpha_{a2})}}{P_2^{\alpha_{a1}} \cdot P_1^{-\alpha_{a2}}}\right] \end{cases}$$

$$\begin{cases} h_a \cdot (\alpha_{a1} \cdot \alpha_{p2} - \alpha_{a2} \cdot \alpha_{p1}) = (\alpha_{p2} - \alpha_{p1}) \cdot \ln P_0 - \ln(P_1^{\alpha_{p2}} \cdot P_2^{-\alpha_{p1}}) \\ h_p \cdot (\alpha_{a1} \cdot \alpha_{p2} - \alpha_{a2} \cdot \alpha_{p1}) = (\alpha_{a1} - \alpha_{a2}) \cdot \ln P_0 - \ln(P_2^{\alpha_{a1}} \cdot P_1^{-\alpha_{a2}}) \end{cases}$$

$$\begin{cases} h_a = \frac{(\alpha_{p2} - \alpha_{p1}) \cdot \ln P_0 + \alpha_{p1} \cdot \ln P_2 - \alpha_{p2} \cdot \ln P_1}{(\alpha_{a1} \cdot \alpha_{p2} - \alpha_{a2} \cdot \alpha_{p1})} \\ h_p = \frac{(\alpha_{a1} - \alpha_{a2}) \cdot \ln P_0 + \alpha_{a2} \cdot \ln P_1 - \alpha_{a1} \cdot \ln P_2}{(\alpha_{a1} \cdot \alpha_{p2} - \alpha_{a2} \cdot \alpha_{p1})} \end{cases}$$

Based on the above, combined plates thickness and adhesive thickness can be determined.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for performing non-destructive evaluation (NDE) of a target sample based on optical transmission measurements, comprising:
    directing probe light to transmit through a target sample to produce transmitted probe light;
    using an optical detector to receive the transmitted probe light and to measure optical transmission of the target sample;
    scanning a relative position between the target sample and the probe light to direct the probe light to transmit through the target sample at different locations of the target sample to obtain measurements of optical transmission of the target sample at the different locations as a result of the scanning;
    discriminating measurements of optical transmission of the target sample at the different locations produced by ballistic photons that transmit through the target sample along a straight line and by scattered photons that transmit through the target sample by being scattered away from a straight line; and
    processing the measurements of optical transmission of the target sample at the different locations produced by ballistic photons and by scattered photons to extract information on a structural pattern distribution in the target sample.

2. The method as in claim 1, wherein:
    a variable diaphragm is placed between the target sample and the optical detector to spatially change an aperture of a light path between the target sample and the optical detector to obtain separate measurements of optical transmission of the target sample at the optical detector produced by ballistic photons and by scattered photons, respectively.

3. The method as in claim 2, comprising:
    using the variable diaphragm to allow only ballistic photons to reach the optical detector to measure an optical power of the ballistic photons; and
    subtracting the measured optical power of the ballistic photons from a total optical power measured at the optical detector by allowing all photons from the target sample to reach the optical detector to obtain an optical power of the scattered photons.

4. The method as in claim 1, comprising:
    operating the optical detector to capture a temporal response of the ballistic photons arriving at the optical detector before the scattered photons and a temporal response of the scattered photons arriving at the optical detector after the ballistic photons,
    wherein the temporal responses of the scattered photons and the ballistic photons are used to discriminating measurements of optical transmission of the target sample at the different locations produced by ballistic photons and scattered photons, respectively.

5. The method as in claim 1, comprising:
    adjusting an optical wavelength of the probe light to the target sample to measure optical transmission by the target sample at the optical detector at two different probe light wavelengths; and using the optical transmission power measurements at the two different probe light wavelengths and optical absorption constants of the target sample at the two different probe light wavelengths to determine, based on a relationship between a scattering signal strength and a light wavelength under the Rayleigh scattering, a portion of the ballistic photons and a portion of the scattered photons in the photons that transmit through the target sample to reach the optical detector.

6. The method as in claim 1, comprising:

adjusting an optical wavelength of the probe light to the target sample to measure optical transmission by the target sample at the optical detector at two or more different probe light wavelengths; and extracting different optical transmission responses of the target sample at the two or more different probe light wavelengths to extract different structural defects in the target sample.

7. The method as in claim 1, comprising:

using a 1-dimensional line shaped light source or 2-dimensional planar shaped light source to produce the probe light to reduce scanning time in optical transmission measurements.

8. The method as in claim 1, comprising:

focusing the probe light when scanning the relative position between the target sample and the probe light; and adjusting a focus position of the focused probe light along a direction of the probe light to be at different focus positions during the scanning to obtain a 3-dimensional measurements of the optical transmission of the target sample to detect different defects at different depths of the target sample.

9. A method for performing non-destructive evaluation (NDE) of a target sample on optical transmission measurements, comprising:

directing probe light at different optical inspection wavelengths to transmit through a target sample to produce transmitted probe light at the different optical inspection wavelengths;

using an optical detector to receive the transmitted probe light at the different optical inspection wavelengths and to measure optical transmission of the target sample at the different optical inspection wavelengths;

scanning a relative position between the target sample and the probe light to direct the probe light to transmit through the target sample at different locations of the target sample to obtain measurements of optical transmission of the target sample at the different optical inspection wavelengths and at the different locations as a result of the scanning;

processing measurements of optical transmission of the target sample at the different locations and at the different optical inspection wavelengths to extract information on a structural pattern distribution in the target sample separating measurements of optical transmission of the target sample at the different locations produced by ballistic photons that transmit through the target sample along a straight line and by scattered photons that transmit through the target sample by being scattered away from a straight line; and processing the measurements of optical transmission of the target sample at the different locations produced by ballistic photons and by scattered photons to extract information on a structural pattern distribution in the target sample.

10. The method as in claim 9, comprising:

placing a variable diaphragm between the target sample and the optical detector to spatially change an aperture of a light path between the target sample and the optical detector to obtain separate measurements of optical transmission of the target sample at the optical detector produced by ballistic photons and by scattered photons, respectively.

11. The method as in claim 9, comprising:

operating the optical detector to capture a temporal response of the ballistic photons arriving at the optical detector before the scattered photons and a temporal response of the scattered photons arriving at the optical detector after the ballistic photons, wherein the temporal responses of the scattered photons and the ballistic photons are used to discriminating measurements of optical transmission of the target sample at the different locations produced by ballistic photons and scattered photons, respectively.

12. A method for performing non-destructive evaluation (NDE) of a target sample on optical transmission measurements, comprising:

directing probe light at different optical inspection wavelengths to transmit through a target sample to produce transmitted probe light at the different optical inspection wavelengths;

using an optical detector to receive the transmitted probe light at the different optical inspection wavelengths and to measure optical transmission of the target sample at the different optical inspection wavelengths;

scanning a relative position between the target sample and the probe light to direct the probe light to transmit through the target sample at different locations of the target sample to obtain measurements of optical transmission of the target sample at the different optical inspection wavelengths and at the different locations as a result of the scanning;

processing measurements of optical transmission of the target sample at the different locations and at the different optical inspection wavelengths to extract information on a structural pattern distribution in the target sample adjusting an optical inspection wavelength of the probe light to the target sample to measure optical transmission by the target sample at the optical detector at two different probe light wavelengths; and using the optical transmission power measurements at the two different probe light wavelengths and optical absorption constants of the target sample at the two different probe light wavelengths to determine, based on a relationship between a scattering signal strength and a light wavelength under the Rayleigh scattering, a portion of the ballistic photons that transmit through the target sample along a straight line and a portion of the scattered photons that transmit through the target sample by being scattered away from a straight line in the photons that transmit through the target sample to reach the optical detector.

13. The method as in claim 9, comprising:

extracting different optical transmission responses of the target sample at the two or more different inspection wavelengths to extract different structural defects in the target sample.

14. The method as in claim 9, comprising:
using a 1-dimensional line shaped light source or 2-dimensional planar shaped light source to produce the probe light to reduce scanning time in optical transmission measurements.

15. The method as in claim 9, comprising:
focusing the probe light when scanning the relative position between the target sample and the probe light; and
adjusting a focus position of the focused probe light along a direction of the probe light to be at different focus positions during the scanning to obtain a 3-dimensional measurements of the optical transmission of the target sample to detect different defects at different depths of the target sample.

16. A method for performing non-destructive evaluation (NDE) of a target sample on optical transmission measurements, comprising:
directing probe light at different optical inspection wavelengths to transmit through a target sample to produce transmitted probe light at the different optical inspection wavelengths;
using an optical detector to receive the transmitted probe light at the different optical inspection wavelengths and to measure optical transmission of the target sample at the different optical inspection wavelengths;
scanning a relative position between the target sample and the probe light to direct the probe light to transmit through the target sample at different locations of the target sample to obtain measurements of optical transmission of the target sample at the different optical inspection wavelengths and at the different locations as a result of the scanning;
processing measurements of optical transmission of the target sample at the different locations and at the different optical inspection wavelengths to extract information on a structural pattern distribution in the target sample;
estimating threshold levels for determining maximal and minimal amplitudes of transmitted photons of a histogram of defect-free regions in the target sample; and
computing contour margins of delaminations in the target sample based on an optical transmission property of a reference sample that has a single delamination.

17. The method as in claim 12, comprising:
placing a variable diaphragm between the target sample and the optical detector to spatially change an aperture of a light path between the target sample and the optical detector to obtain separate measurements of optical transmission of the target sample at the optical detector produced by ballistic photons and by scattered photons, respectively.

18. The method as in claim 12, comprising:
operating the optical detector to capture a temporal response of the ballistic photons arriving at the optical detector before the scattered photons and a temporal response of the scattered photons arriving at the optical detector after the ballistic photons,
wherein the temporal responses of the scattered photons and the ballistic photons are used to discriminating measurements of optical transmission of the target sample at the different locations produced by ballistic photons and scattered photons, respectively.

19. The method as in claim 16, comprising:
placing a variable diaphragm between the target sample and the optical detector to spatially change an aperture of a light path between the target sample and the optical detector to obtain separate measurements of optical transmission of the target sample at the optical detector produced by ballistic photons and by scattered photons, respectively.

20. The method as in claim 16, comprising:
operating the optical detector to capture a temporal response of the ballistic photons arriving at the optical detector before the scattered photons and a temporal response of the scattered photons arriving at the optical detector after the ballistic photons,
wherein the temporal responses of the scattered photons and the ballistic photons are used to discriminating measurements of optical transmission of the target sample at the different locations produced by ballistic photons and scattered photons, respectively.

* * * * *